US012691439B2

(12) United States Patent (10) Patent No.: US 12,691,439 B2
Nagata et al. (45) Date of Patent: Jul. 28, 2026

(54) CATALYST FOR PRODUCTION OF CARBOXYLIC ACID ESTER AND METHOD FOR PRODUCING CARBOXYLIC ACID ESTER

(71) Applicant: ASAHI KASEI KABUSHIKI KAISHA, Tokyo (JP)

(72) Inventors: Dai Nagata, Tokyo (JP); Hitoshi Okazaki, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 587 days.

(21) Appl. No.: 18/024,728

(22) PCT Filed: Sep. 4, 2020

(86) PCT No.: PCT/JP2020/033660
§ 371 (c)(1),
(2) Date: Mar. 3, 2023

(87) PCT Pub. No.: WO2022/049740
PCT Pub. Date: Mar. 10, 2022

(65) Prior Publication Data
US 2023/0311103 A1 Oct. 5, 2023

(51) Int. Cl.
| *B01J 23/89* | (2006.01) |
| *B01J 23/62* | (2006.01) |
| *B01J 35/30* | (2024.01) |
| *B01J 35/40* | (2024.01) |
| *B01J 35/45* | (2024.01) |
| *B01J 35/64* | (2024.01) |
| *B01J 35/77* | (2024.01) |
| *C07C 67/39* | (2006.01) |

(52) U.S. Cl.
CPC ........... *B01J 23/892* (2013.01); *B01J 23/628* (2013.01); *B01J 23/8913* (2013.01); *B01J 35/393* (2024.01); *B01J 35/40* (2024.01); *B01J 35/45* (2024.01); *B01J 35/643* (2024.01); *B01J 35/647* (2024.01); *B01J 35/77* (2024.01); *C07C 67/39* (2013.01); *B01J 2235/00* (2024.01); *B01J 2235/15* (2024.01); *B01J 2235/30* (2024.01)

(58) Field of Classification Search
CPC .... B01J 23/892; B01J 23/628; B01J 23/8913; B01J 35/40; B01J 34/45; B01J 35/643; B01J 35/647; C07C 67/39; C07C 67/42; C07C 69/54
See application file for complete search history.

(56) References Cited

U.S. PATENT DOCUMENTS

| 3,436,358 A | 4/1969 | Thygesen et al. |
| 3,901,827 A | 8/1975 | Sinfelt et al. |
| 3,953,363 A | 4/1976 | Yamauchi et al. |
| 4,035,263 A | 7/1977 | Umemura et al. |
| 4,374,046 A | 2/1983 | Antos |
| 4,518,796 A | 5/1985 | Aoshima et al. |
| 4,536,482 A | 8/1985 | Carcia |
| 4,562,174 A | 12/1985 | Stiles |
| 4,698,324 A | 10/1987 | Haruta et al. |
| 4,711,870 A | 12/1987 | Yamada et al. |
| 4,959,338 A | 9/1990 | Miura et al. |
| 4,992,408 A | 2/1991 | Jackson |
| 5,002,922 A | 3/1991 | Irgang et al. |
| 5,094,996 A | 3/1992 | Kidd |
| 5,128,114 A | 7/1992 | Schwartz |
| 5,254,705 A | 10/1993 | Hattori et al. |
| 5,347,046 A | 9/1994 | White et al. |
| 5,472,928 A | 12/1995 | Scheuerman et al. |
| 5,494,879 A | 2/1996 | Jin et al. |
| 5,506,273 A | 4/1996 | Haruta et al. |
| 5,883,036 A | 3/1999 | Fujie et al. |
| 6,057,442 A | 5/2000 | Wulff-Döring et al. |
| 6,103,894 A | 8/2000 | Degelmann et al. |
| 6,228,800 B1 | 5/2001 | Yamaguchi et al. |
| 6,432,868 B1 | 8/2002 | Marchal-George et al. |
| 6,514,905 B1 | 2/2003 | Hanaki et al. |
| 6,635,191 B2 | 10/2003 | Figueroa et al. |
| 6,660,897 B1 | 12/2003 | Marchal-George et al. |

(Continued)

FOREIGN PATENT DOCUMENTS

| CN | 1123527 A | 5/1996 |
| CN | 1512915 A | 7/2004 |

(Continued)

OTHER PUBLICATIONS

Han et al., "Modified extra-large mesoporous silica supported Au—Ni as a highly efficient catalyst for oxidative coupling of aldehydes with methanol," RSC Advances, vol. 4, 2014, pp. 58769-58772, 11 pages total.
Suzuki et al., "Aerobic Oxidative Esterification of Aldehydes with Alcohols by Gold-Nickel Oxide Nanoparticle Catalysts with a Core-Shell Structure," ACS Catalysis, vol. 3, 2013, pp. 1845-1849 and S1-S12.
Anandharamakrishnan et al., "Spray Drying Techniques for Food Ingredient Encapsulation," John Wiley & Sons, Ltd., First Edition, 2015, pp. 1-36.

(Continued)

*Primary Examiner* — Jafar F Parsa
(74) *Attorney, Agent, or Firm* — Birch, Stewart, Kolasch & Birch, LLP

(57) ABSTRACT

A catalyst for production of carboxylic acid ester, containing:
catalyst particles containing at least one element selected from the group consisting of nickel, cobalt, palladium, lead, platinum, ruthenium, gold, silver, and copper; and
a support supporting the catalyst particles, wherein
the catalyst for production of carboxylic acid ester has half-width Wa of pore distribution of 10 nm or less, the half-width Wa being calculated using BJH method from an adsorption isotherm obtained by nitrogen adsorption.

24 Claims, 1 Drawing Sheet

(56) References Cited

U.S. PATENT DOCUMENTS

| | | | |
|---|---|---|---|
| 6,706,659 B2 | 3/2004 | Gillespie et al. | |
| 6,723,678 B2 | 4/2004 | Gorer | |
| 6,846,471 B2 | 1/2005 | Hotta et al. | |
| 6,861,387 B2 | 3/2005 | Ruth et al. | |
| 6,921,605 B2 | 7/2005 | Gorer | |
| 6,930,073 B2 | 8/2005 | Dou | |
| 7,005,059 B1 | 2/2006 | Quartararo et al. | |
| 7,005,405 B2 | 2/2006 | Suenaga et al. | |
| 7,105,107 B2 | 9/2006 | Ramani et al. | |
| 7,109,145 B2 | 9/2006 | Ruth et al. | |
| 7,119,045 B2 | 10/2006 | Magna et al. | |
| 7,176,159 B1 | 2/2007 | Wheelock et al. | |
| 7,268,097 B2 | 9/2007 | Katsuno et al. | |
| 7,361,626 B2 | 4/2008 | Baijense et al. | |
| 7,422,995 B2 | 9/2008 | Baijense et al. | |
| 7,528,092 B2 | 5/2009 | Berben et al. | |
| 7,662,740 B2 | 2/2010 | Chondroudis et al. | |
| 7,811,965 B2 | 10/2010 | Cendak et al. | |
| 8,450,235 B2 | 5/2013 | Suzuki et al. | |
| 2001/0025008 A1 | 9/2001 | Hu et al. | |
| 2002/0062039 A1 | 5/2002 | Salem et al. | |
| 2003/0040635 A1 | 2/2003 | Jansen et al. | |
| 2003/0060655 A1 | 3/2003 | Hayashi et al. | |
| 2004/0238410 A1 | 12/2004 | Inoue et al. | |
| 2005/0054792 A1 | 3/2005 | Kilty et al. | |
| 2005/0131255 A1 | 6/2005 | Benderly et al. | |
| 2006/0014980 A1 | 1/2006 | Kawato et al. | |
| 2006/0084830 A1 | 4/2006 | Ryu | |
| 2007/0021629 A1 | 1/2007 | Stevenson et al. | |
| 2007/0179320 A1 | 8/2007 | Hirota et al. | |
| 2007/0191651 A1 | 8/2007 | Coupard et al. | |
| 2008/0177111 A1 | 7/2008 | van Laar et al. | |
| 2008/0242537 A1 | 10/2008 | Kubanek et al. | |
| 2008/0286176 A1 | 11/2008 | Schirmeister et al. | |
| 2009/0221849 A1 | 9/2009 | Begli et al. | |
| 2010/0029980 A1 | 2/2010 | Johnston et al. | |
| 2010/0249448 A1* | 9/2010 | Suzuki | B01J 35/393 |
| | | | 502/259 |
| 2011/0184206 A1 | 7/2011 | Suzuki et al. | |
| 2013/0172599 A1* | 7/2013 | Suzuki | B01J 23/8896 |
| | | | 502/262 |
| 2018/0326400 A1 | 11/2018 | Lygin et al. | |
| 2019/0084914 A1 | 3/2019 | Krill et al. | |
| 2019/0262800 A1 | 8/2019 | Nagata et al. | |
| 2019/0358613 A1 | 11/2019 | Ernst et al. | |
| 2020/0061590 A1 | 2/2020 | Tomoda et al. | |
| 2020/0165196 A1 | 5/2020 | Nagata et al. | |

FOREIGN PATENT DOCUMENTS

| | | | |
|---|---|---|---|
| CN | 1915475 A | 2/2007 |
| CN | 107519892 A | 12/2017 |
| CN | 108126762 A | 6/2018 |
| CN | 109046259 A | 12/2018 |
| CN | 109562356 A | 4/2019 |
| CN | 109821529 A | 5/2019 |
| CN | 110248729 A | 9/2019 |
| CN | 111072810 A | 4/2020 |
| DE | 10 2005 041 532 A1 | 3/2007 |
| DE | 10 2007 004 558 A1 | 8/2007 |
| EP | 1 283 206 A2 | 2/2003 |
| EP | 1 459 803 A1 | 9/2004 |
| EP | 1 495 802 A1 | 1/2005 |
| EP | 1 518 600 A1 | 3/2005 |
| EP | 1 358 935 B1 | 9/2007 |
| EP | 2 177 267 A1 | 4/2010 |
| EP | 2 210 664 A1 | 7/2010 |
| EP | 2 617 679 A1 | 7/2013 |
| EP | 3 626 338 A1 | 3/2020 |
| FR | 2 882 531 A1 | 9/2006 |
| GB | 1 415 636 A1 | 11/1975 |
| JP | 45-34368 B | 11/1970 |
| JP | 55-153743 U | 11/1980 |
| JP | 60-96522 A | 5/1985 |
| JP | 62-7902 B2 | 2/1987 |
| JP | 62-27041 A | 2/1987 |
| JP | 6-256011 A | 9/1994 |
| JP | 7-47273 A | 2/1995 |
| JP | 7-313880 A | 12/1995 |
| JP | 8-57323 A | 3/1996 |
| JP | 8-215544 A | 8/1996 |
| JP | 9-52044 A | 2/1997 |
| JP | 9-286662 A | 11/1997 |
| JP | 11-1490 A | 1/1999 |
| JP | 2000-95514 A | 4/2000 |
| JP | 2000-154164 A | 6/2000 |
| JP | 2000-176285 A | 6/2000 |
| JP | 2001-79402 A | 3/2001 |
| JP | 2001-172222 A | 6/2001 |
| JP | 2001-220367 A | 8/2001 |
| JP | 2002-282876 A | 10/2002 |
| JP | 2002-361086 A | 12/2002 |
| JP | 2003-53188 A | 2/2003 |
| JP | 2003-103174 A | 4/2003 |
| JP | 2003-192632 A | 7/2003 |
| JP | 2003-521364 A | 7/2003 |
| JP | 2003-305366 A | 10/2003 |
| JP | 2004-141828 A | 5/2004 |
| JP | 2004-209406 A | 7/2004 |
| JP | 2004-209408 A | 7/2004 |
| JP | 2004-351364 A | 12/2004 |
| JP | 2006-212571 A | 8/2006 |
| JP | 2006-240920 A | 9/2006 |
| JP | 2006-265361 A | 10/2006 |
| JP | 2007-197396 A | 8/2007 |
| JP | 2007-245068 A | 9/2007 |
| JP | 2008-538323 A | 10/2008 |
| JP | 2009-502491 A | 1/2009 |
| JP | 4420991 B2 | 2/2010 |
| JP | 2010-221081 A | 10/2010 |
| JP | 2010-221082 A | 10/2010 |
| JP | 2010-221083 A | 10/2010 |
| JP | 2010-222151 A | 10/2010 |
| JP | 4674921 B2 | 4/2011 |
| JP | 4803767 B2 | 10/2011 |
| JP | 2011-529493 A | 12/2011 |
| JP | 5335505 B2 | 11/2013 |
| JP | 5336234 B2 | 11/2013 |
| JP | 5336235 B2 | 11/2013 |
| JP | 2016-686 A | 1/2016 |
| JP | 2018-535825 A | 12/2018 |
| JP | 2019-1775 A | 1/2019 |
| JP | 2020-1001 A | 1/2020 |
| KR | 10-2010-0019569 A | 2/2010 |
| TW | 200613053 A | 5/2006 |
| TW | 200914130 A | 4/2009 |
| WO | WO 00/43121 A1 | 7/2000 |
| WO | WO 2004/011138 A1 | 2/2004 |
| WO | WO 2005/037768 A1 | 4/2005 |
| WO | WO 2006/064685 A1 | 6/2006 |
| WO | WO 2006/079850 A1 | 8/2006 |
| WO | WO 2007/015620 A1 | 2/2007 |
| WO | WO 2009/022544 A1 | 2/2009 |
| WO | WO 2009/054462 A1 | 4/2009 |
| WO | WO 2012/035637 A1 | 3/2012 |
| WO | WO 2017/084969 A1 | 5/2017 |
| WO | WO 2018/030384 A1 | 2/2018 |
| WO | WO 2018/235798 A1 | 12/2018 |

OTHER PUBLICATIONS

Barrio et al., "Evaluation of Silica-Alumina-Supported Nickel Catalysts in Dibenzothiophene Hydrodesulphurisation," Applied Catalysis A: General, vol. 248, 2003, pp. 211-225.

Castano et al, "Enhancement of pyrolysis gasoline hydrogenation over Pd-promoted Ni/SIO2—Al2O3 catalysts," Fuel, vol. 86, 2007, pp. 2262-2274.

Chinese Office Action for Chinese Application No. 200880102565.3 dated Mar. 1, 2012.

Chinese Office Action for Chinese Application No. 200880112821.7 dated Feb. 22, 2012.

(56)　　　　　References Cited

OTHER PUBLICATIONS

Chinese Office Action for Chinese Application No. 200880112821. 7, dated Nov. 27, 2012.

Choudary et al., "The First Example of Activation of Molecular Oxygen by Nickel in Ni—Al Hydrotalcite: A Novel Protocol for the Selective Oxidation of Alcohols," Angewandte Chemie Int. Ed., vol. 40, No. 4, 2001, pp. 763-766.

Dai et al., "Photodegradation Catalyst Screening by Combinatorial Methodology," Applied Catalysis A: General, vol. 290, 2005, pp. 25-35.

Eckhard et al., "Variation der Produkteigenschaften sprühgetrockneter Nanoskaliger SiO2-Granulate," Symposium Produktgestaltung in der Partikeltechnologie 2011, 2011, URL: <https://publicarest. fraunhofer.de/server/api/core/bitstreams/030023a4-5670-461b-9256-32a6b755ae7e/content>.

Eckhard et al., "Variation of Product Properties of Granules Spray-Dried From Nanoscale SiO2", Chemie Ingenieur Technik, vol. 84, No. 3, 2012, pp. 335-342, with an English abstract.

English translation of International Preliminary Report on Patentability and Written Opinion of the International Searching Authority for International Application No. PCT/JP2010/066084, dated Apr. 9, 2013.

English translation of the International Search Report for International Application No. PCT/JP2008/069249, dated Mar. 3, 2009.

English translation of the International Search Report for International Application No. PCT/JP2010/066084, dated Dec. 21, 2010.

European Search Report for European Application No. 08791982. 5-1270, dated Nov. 7, 2011.

European Search Report for European Application No. 08841939. 5-1270, dated Nov. 17, 2011.

European Search Report for European Application No. 10857271.0, dated Feb. 2, 2015.

European Search Report for European Application No. 21760142.6, dated Jul. 13, 2023.

Ferreira et al., "Theoretical optical properties of composite metal-NiO films," Journal of Physics D: Applied Physics, vol. 36, 2003, pp. 2386-2392.

Fuson et al., "Double Bond Migration in 1,2-Diaroyl-1-cycloalkenes," The Journal of Organic Chemistry, vol. 27, No. 5, May 1962, pp. 1957-1961.

Grisel et al., "A Comparative Study of the Oxidation of CO and CH4 Over Au/MOx/Al2O3 Catalysts," Catalysis Today, vol. 64, 2001, pp. 69-81.

International Preliminary Report on Patentability and English translation of the Written Opinion of the International Searching Authority for International Application No. PCT/JP2008/063767, dated Mar. 9, 2010.

International Preliminary Report on Patentability and English translation of the Written Opinion of the International Searching Authority for International Application No. PCT/JP2008/069249, dated Jun. 1, 2010.

International Preliminary Report on Patentability and English translation of the Written Opinion of the International Searching Authority for International Application No. PCT/JP2021/007189, dated Sep. 9, 2022.

International Preliminary Report on Patentability and Written Opinion of the International Searching Authority for International Application No. PCT/JP2021/013068, dated Oct. 5, 2023, with an English translation.

International Search Report for International Application No. PCT/JP2021/013068, dated May 25, 2021, with an English translation.

International Search Report, issued in PCT/JP2021/007189, dated Apr. 27, 2021.

Japanese Office Action for Japanese Patent Application No. 2009-068421, dated Jul. 30, 2013.

Japanese Office Action for Japanese Patent Application No. 2009-257201, dated Dec. 6, 2013.

Ji et al., "Simple Fabrication of Nano-Sized NiO2 Powder and Its Application to Oxidation Reactions," Applied Catalysis A: General, vol. 282, 2005, pp. 25-30.

Kawabata et al., "Nickel Containing Mg—Al hydrotalcite-type anionic clay catalyst for the oxidation of alcohols with molecular oxygen," Journal of Molecular Catalysis A: Chemical, vol. 236, 2005, pp. 206-215.

Korean Office Action for Korean Patent Application No. 10-2013-7003812, dated Apr. 22, 2014.

Nakagawa et al., "Oxidation with Nickel Peroxide. I. Oxidation of Alcohols," The Journal of Organic Chemistry, vol. 27, No. 5, May 1962, pp. 1597-1601.

Okuda et al., "Preparation of Ag—NiO Composite Powders by Spray Pyrolysis from AG and NI Loading Versatic Acid 10," Resources and Materials, vol. 118, 2002, pp. 91-94 (22 pages total).

Supplementary European Search Report for European Application No. 21933136.0, dated Apr. 19, 2024.

Taiwanese Office Action and Search Report for Taiwanese Application No. 097130712, dated Jul. 30, 2012.

Taiwanese Office Action and Search Report for Taiwanese Application No. 097140722, dated Sep. 27, 2012.

Third Party Observation for European Application No. 21760142.6, dated Jul. 5, 2024.

U.S. Office Action for U.S. Appl. No. 17/802,610, dated Mar. 20, 2025.

Written Opinion of the International Searching Authority, issued in PCT/JP2021/007189, dated Apr. 27, 2021.

European Office Action for European Application No. 20952475.0, dated Aug. 29, 2023.

International Preliminary Report on Patentability and Written Opinion of the International Searching Authority for International Application No. PCT/JP2020/033660, dated Mar. 16, 2023, with an English translation.

International Search Report for International Application No. PCT/JP2020/033660, dated Nov. 17, 2020, with an English translation.

* cited by examiner

[Figure 1]
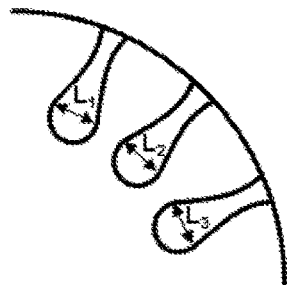
[Figure 2]
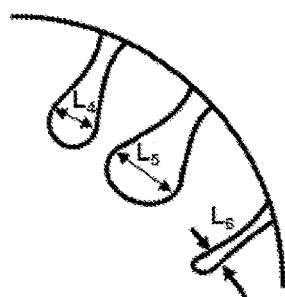
[Figure 3]
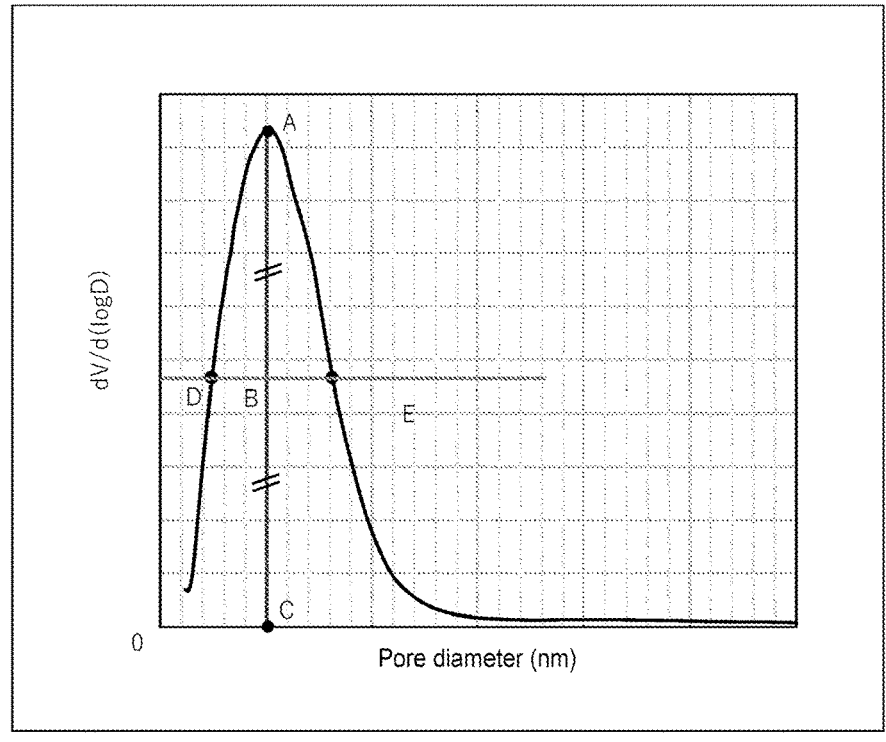

CATALYST FOR PRODUCTION OF CARBOXYLIC ACID ESTER AND METHOD FOR PRODUCING CARBOXYLIC ACID ESTER

TECHNICAL FIELD

The present invention relates to a catalyst for production of carboxylic acid ester and a method for producing carboxylic acid ester.

BACKGROUND ART

Nickel or nickel compounds are widely used as catalysts for chemical synthesis such as oxidation reactions, reduction reactions, or hydrogenation reactions. In recent years, catalytic oxygen oxidation reactions of alcohols have been realized by various modifications or improvements of nickel-based catalysts. Incidentally, such nickel and nickel compounds are known in the chemical industry to be widely effective not only for the oxidation reactions of alcohols but also for various reactions such as various oxidation reactions, reduction reactions, and hydrogenation reactions, and for purification catalysts for vehicle emissions, photocatalysts, and the like.

For example, in Patent Literature 1, as a method for producing carboxylic acid ester, there is suggested use of a composite particle supported material as a catalyst, the composite particle supported material comprising: composite particles constituted by oxidized nickel and X (wherein X represents at least one element selected from the group consisting of nickel, palladium, platinum, ruthenium, gold, silver, and copper); and a support supporting the composite particles, wherein the composite particle supported material has a supported layer in which the composite particles are localized. The catalyst is reported to be capable of maintaining high reactivity over a long period. In Patent Literature 1, for a support applicable to such a catalyst, it is reported that a pore structure can be adjusted by performing predetermined aging. Likewise, in Patent Literature 2, it is reported that a support having a uniform pore structure so as to have a pore diameter of most pores within a narrow range of from 3 to 5 nm can be obtained through a predetermined hydrothermal treatment.

CITATION LIST

Patent Literature

Patent Literature 1: Japanese Patent No. 4803767
Patent Literature 2: Japanese Patent No. 5794993

SUMMARY OF INVENTION

Technical Problem

In production of carboxylic acid ester using the catalyst described in Patent Literature 1 or 2, since methacrylic acid is generated as a by-product, pH is decreased during reaction and as a result, the activity of the catalyst tends to be reduced. In consideration of such a tendency, it may be possible that pH of the reaction system is controlled to a predetermined range, for example, by adding a basic substance thereto. However, the addition of the basic substance is also supposed to locally elevate pH in the reaction system. When long-term use for several years in the reaction system as described above is taken into consideration, the catalyst is required to improve acid resistance and base resistance (hereinafter, also referred to as "pH swing resistance") ascribable to a fluctuating behavior of pH (hereinafter, also referred to as "pH swing").

The production of carboxylic acid ester can be carried out at relatively low temperatures. However, when long-term use for several years is taken into consideration, the activity or selectivity of the catalyst may be reduced due to exposure to relatively high temperature conditions. Thus, temperature resistance is also demanded.

As described above, when the long-term use of the catalyst for several years is expected, it is desirable to improve durability which also takes pH swing resistance and/or temperature resistance into consideration (hereinafter, also simply referred to as "durability"). However, the technique described in Patent Literature 1 or 2 is still susceptible to improvement in this durability.

The present invention has been accomplished in light of the above problems involved in the conventional art, and it is an object thereof to provide a catalyst for production of carboxylic acid ester, the catalyst being excellent in durability expected for long-term use.

Solution to Problem

As a result of conducting studies, the present inventors have completed the present invention by finding that durability expected for long-term use is improved by setting a half-width of pore diameter distribution of a catalyst for production of carboxylic acid ester, which is measured by a predetermined method, to a predetermined range so that variation in pore diameter inside pores of a support is suppressed.

That is, the present invention encompasses aspects as follows.

[1]

A catalyst for production of carboxylic acid ester comprising:

catalyst particles comprising at least one element selected from the group consisting of nickel, cobalt, palladium, lead, platinum, ruthenium, gold, silver, and copper; and a support supporting the catalyst particles, wherein the catalyst for production of carboxylic acid ester has a half-width Wa of pore distribution of 10 nm or less, the half-width Wa being calculated using BJH method from an adsorption isotherm obtained by nitrogen adsorption.

[2]

The catalyst for production of carboxylic acid ester according to [1], wherein the catalyst for production of carboxylic acid ester has a half-width Wd of pore distribution of 5 nm or less, the half-width Wd being calculated using BJH method from a desorption isotherm obtained by nitrogen adsorption.

[3]

The catalyst for production of carboxylic acid ester according to [1] or [2], wherein the catalyst for production of carboxylic acid ester has a pore mode diameter Da of 2 nm or more and 20 nm or less, the pore mode diameter Da being calculated using BJH method from an adsorption isotherm obtained by nitrogen adsorption.

[4]

The catalyst for production of carboxylic acid ester according to any of [1] to [3], wherein the pore mode diameter Da and the half-width Wa of the catalyst for production of carboxylic acid ester, the pore mode diameter Da and the half-width Wa being calculated using BJH method from the adsorption isotherm obtained by nitrogen adsorption, satisfy a relationship of the following expression (1):

$$\tfrac{1}{2}Wa < Da \qquad (1)$$

[5]

The catalyst for production of carboxylic acid ester according to any of [1] to [4], wherein the catalyst for production of carboxylic acid ester has a pore mode diameter Dd of 2 nm or more and 15 nm or less, the pore mode diameter Dd being calculated using BJH method from a desorption isotherm obtained by nitrogen adsorption.

[6]

The catalyst for production of carboxylic acid ester according to any of [1] to [5], wherein a pore mode diameter Dd of the catalyst for production of carboxylic acid ester, the pore mode diameter Dd being calculated using BJH method from a desorption isotherm obtained by nitrogen adsorption, and a half-width Wd of pore distribution of the catalyst for production of carboxylic acid ester, the half-width Wd being calculated using BJH method from a desorption isotherm obtained by nitrogen adsorption, satisfy a relationship of the following expression (2):

$$\tfrac{1}{2}Wd < Dd \qquad (2)$$

[7]

The catalyst for production of carboxylic acid ester according to any of [1] to [6], wherein the half-width Wa is 0.1 nm or more.

[8]

The catalyst for production of carboxylic acid ester according to any of [1] to [7], wherein the catalyst particles comprise at least one element selected from the group consisting of nickel, cobalt, palladium, lead, and gold.

[9]

The catalyst for production of carboxylic acid ester according to any of [1] to [8], wherein the catalyst particles are composite particles comprising:

oxidized nickel and/or cobalt, and

X, wherein X represents at least one element selected from the group consisting of nickel, palladium, platinum, ruthenium, gold, silver, and copper.

[10]

The catalyst for production of carboxylic acid ester according to [9], wherein a compositional ratio between nickel or cobalt and X in the composite particles, in terms of a Ni/X atomic ratio or a Co/X atomic ratio, is 0.1 or more and 10 or less.

[11]

The catalyst for production of carboxylic acid ester according to [9], wherein the composite particles comprise oxidized nickel and gold.

[12]

The catalyst for production of carboxylic acid ester according to [10], wherein a compositional ratio between nickel and gold in the composite particles, in terms of a Ni/Au atomic ratio, is 1.1 or more and 10 or less.

[13]

The catalyst for production of carboxylic acid ester according to any of [1] to [12], wherein the catalyst particles have an average particle diameter of 2 nm or more and 10 nm or less.

[14]

The catalyst for production of carboxylic acid ester according to any of [1] to [13], wherein the support is a support composed of aluminum-containing silica-based composition comprising silica and alumina.

[15]

The catalyst for production of carboxylic acid ester according to any of [1] to [14], wherein the support is a silica-based material comprising:

silicon, aluminum, at least one period 4 element selected from the group consisting of iron, cobalt, nickel, and zinc, and at least one basic element selected from the group consisting of an alkali metal element, an alkaline earth metal element, and a rare earth element, wherein contents thereof are in ranges of 42 mol % or more and 90 mol % or less, 3 mol % or more and 38 mol % or less, 0.5 mol % or more and 20 mol % or less, and 2 mol % or more and 38 mol % or less, respectively, based on a total molar amount of the silicon, the aluminum, the period 4 element, and the basic element.

[16]

The catalyst for production of carboxylic acid ester according to any of [1] to [15], wherein a supported layer in which the catalyst particles are localized is present in a region extending from a surface of the catalyst for production of carboxylic acid ester to 40% of an equivalent diameter of the catalyst for production of carboxylic acid ester.

[17]

The catalyst for production of carboxylic acid ester according to any of [1] to [16], wherein the catalyst for production of carboxylic acid ester has an equivalent diameter of 200 μm or less, and a supported layer in which the catalyst particles are localized is present in a region extending from the surface of the catalyst for production of carboxylic acid ester to 30% of the equivalent diameter of the catalyst for production of carboxylic acid ester.

[18]

The catalyst for production of carboxylic acid ester according to any of [1] to [17], wherein the catalyst for production of carboxylic acid ester has an outer layer substantially free of catalyst particles on an outside of the supported layer in which the catalyst particles are localized, and the outer layer is formed at a thickness of 0.01 μm or more and 15 μm or less.

[19]

The catalyst for production of carboxylic acid ester according to any of [9] to [18], wherein the catalyst particles have a core composed of X, and the core is coated with oxidized nickel and/or cobalt.

[20]

A method for producing carboxylic acid ester comprising a reaction step of reacting (a) an aldehyde and an alcohol or (b) one or two or more alcohols in a presence of the catalyst for production of carboxylic acid ester according to any of [1] to [19] and oxygen.

[21]

The method for producing carboxylic acid ester according to [20], wherein the aldehyde is acrolein and/or methacrolein.

[22]

The method for producing carboxylic acid ester according to [20] or [21], wherein the aldehyde is acrolein and/or methacrolein, and the alcohol is methanol.

[23]

The method for producing carboxylic acid ester according to any of [20] to [22], wherein the reaction step is performed in a liquid phase.

[24]

The method for producing carboxylic acid ester according to any of [20] to [23], wherein the reaction step is performed while a basic substance is added so that pH of the reaction system is 6 or more and 8 or less.

Advantageous Effects of Invention

According to the present invention, a catalyst for production of carboxylic acid ester that is excellent in durability expected for long-term use can be provided.

BRIEF DESCRIPTION OF DRAWINGS

FIG. 1 shows a cross-sectional schematic view showing a typical example of a pore structure of a catalyst for production of carboxylic acid ester according to one embodiment of the present invention.

FIG. 2 shows a cross-sectional schematic view showing a typical example of a pore structure of a conventional catalyst.

FIG. 3 shows a conceptual diagram showing how to determine a half-width.

DESCRIPTION OF EMBODIMENT

Hereinbelow, an embodiment of the present invention (hereinbelow, referred to as "the present embodiment") will be described in detail. The present invention is not limited to the following present embodiment, and can be variously modified and implemented without departing from the gist.

[Catalyst for Production of Carboxylic Acid Ester]

A catalyst for production of carboxylic acid ester of the present embodiment is a catalyst for production of carboxylic acid ester comprising: catalyst particles comprising at least one element selected from the group consisting of nickel, cobalt, palladium, lead, platinum, ruthenium, gold, silver, and copper; and a support supporting the catalyst particles, wherein the catalyst for production of carboxylic acid ester has a half-width Wa of pore distribution of 10 nm or less, the half-width Wa being calculated using BJH method from an adsorption isotherm obtained by nitrogen adsorption. Being thus configured, the catalyst for production of carboxylic acid ester of the present embodiment is excellent in durability expected for long-term use. More specifically, the catalyst for production of carboxylic acid ester of the present embodiment is excellent in, for example, pH swing resistance and/or temperature resistance.

The pore structure of the catalyst for production of carboxylic acid ester of the present embodiment can be derived from pores of the support. In the present embodiment, the pore structure is defined by a half-width of pore distribution (hereinafter, also simply referred to as "half-width Wa") calculated using BJH (Barrett, Joyner and Halenda) method from an adsorption isotherm obtained by nitrogen adsorption. With respect to the pore distribution determined by the BJH method, there are two possible methods: a method of obtaining an adsorption isotherm and calculating a pore distribution (pore distribution on the adsorption side); and a method of obtaining a desorption isotherm and calculating a pore distribution (pore distribution on the desorption side). In the latter method, evaluation results that properly reflect pore diameters at or near the inlets of pores are obtained, though the evaluation results do not correctly reflect variation in pore diameter inside the pores. By contrast, in the former method, evaluation results that reflect variation from the inlets to the inside of the pores (true distribution) are obtained and thus serve as a suitable evaluation index for obtaining a support that is uniform from the inlets to the inside of pores. In the present embodiment, the former method is adopted to define the pore structure and to adjust the half-width Wa of pore distribution to 10 nm or less. Therefore, the resulting catalyst for production of carboxylic acid ester has a structure that is uniform from the inlets to the inside of pores (e.g., in the cross-sectional schematic view shown in FIG. 1, diameters $L_1$, $L_2$, and $L_3$ inside pores are uniform values thereamong).

On the other hand, when the half-width Wa is more than 10 nm, variation occurs in pore diameter inside pores (e.g., in the cross-sectional schematic view shown in FIG. 2, diameters $L_4$, $L_5$, and $L_6$ inside pores are values that vary thereamong), even if pore diameters at or near the inlets of the pores are uniform. It is thus difficult to maintain catalyst performance over a sufficiently long period because change in pore structure caused by long-term use becomes evident.

From the above viewpoints, the half-width Wa is 10 nm or less, preferably 8 nm or less, more preferably 7 nm or less, and even more preferably 5 nm or less.

The lower limit value of the half-width Wa is not particularly limited, and may be, for example, 0.1 nm or more, may be 1 nm or more, or may be 3 nm or more.

The value of the half-width Wa is measured by a method described in the examples to be described below.

A method for adjusting the half-width Wa is not particularly limited, and the catalyst for production of carboxylic acid ester can have sufficiently small half-width Wa, for example, by adopting a preferable production method described below. More specifically, it is considered that the sizes of silica chains are easily uniformed by adopting preferable conditions for the production method described below, and preparing a slurry. That is, the uniform pore diameter of silica depends on the sizes of silica chains of a support slurry. The pore diameters are easily uniformed as long as the silica chains have a uniform size. As a result, the uniform size of the silica chains facilitates densifying inner walls constituting the pores. It is thus considered that even if the catalyst is subject to pH swing, increase in the pore diameter of silica is suppressed and pH swing resistance is improved. However, the above idea is a mere possible factor for obtaining the above structure in the catalyst for production of carboxylic acid ester of the present embodiment, and the mechanism of action of the present embodiment is not limited thereto.

In the present embodiment, when the pores of the support have a uniform pore diameter at or near the inlets, the durability of the catalyst against long-term use is more improved than that when the pore diameters are uniformed only inside the pores. As a result, a conversion rate tends to be more improved. From the above viewpoints, a half-width of pore distribution of the catalyst for production of carboxylic acid ester, the half-width being calculated using a BJH method from a desorption isotherm obtained by nitrogen adsorption, is preferably 5 nm or less, more preferably 4 nm or less, and even more preferably 3 nm or less. Hereinafter, said half-width is also simply referred to as "half-width Wd."

The lower limit value of the half-width Wd is not particularly limited, and may be, for example, 0.1 nm or more, may be 1 nm or more, or may be 2 nm or more.

The value of the half-width Wd is measured by a method described in the examples to be described below.

A method for adjusting the half-width Wd is not particularly limited, and the half-width Wd of the catalyst for production of carboxylic acid ester can be adjusted to the above range, for example, by adopting a preferable production method described below.

In the present embodiment, the pore mode diameter Da of the catalyst for production of carboxylic acid ester calculated using a BJH method from an adsorption isotherm obtained by nitrogen adsorption is derived from the pore structure of the support, and is preferably 2 nm or more from the viewpoint of promoting growth of composite particles within pores. On the other hand, the pore mode diameter Da is preferably 20 nm or less from the viewpoint of difficulty in cracking of the catalyst. Thus, the pore inside diameter Da of the catalyst for production of carboxylic acid ester is preferably 2 nm or more and 20 nm or less, more preferably 2 nm or more and 15 nm or less, and even more preferably 3 nm or more and 10 nm or less.

The value of the pore mode diameter Da is measured by a method described in the examples to be described below.

A method for adjusting the pore mode diameter Da is not particularly limited, and the pore mode diameter Da can be adjusted to the above range, for example, by adopting a preferable production method described below.

The half-width Wa and the pore mode diameter Da preferably satisfy a relationship of the following expression (1):

$$\tfrac{1}{2}Wa < Da \qquad (1)$$

In the present embodiment, the pore mode diameter Dd of the catalyst for production of carboxylic acid ester calculated using BJH method from a desorption isotherm obtained by nitrogen adsorption is preferably 2 nm or more from the viewpoints of not making the intrapore diffusion resistance excessively great so as not to cause the diffusion process of the reaction substrate to be rate-limiting as well as of maintaining the reaction activity at a high level. On the other hand, the pore mode diameter Dd is preferably 15 nm or less from the viewpoint of difficulty in cracking of the catalyst. Thus, the pore inlet diameter Dd of the catalyst for production of carboxylic acid ester is preferably 2 nm or more and 15 nm or less, more preferably 2 nm or more and 7 nm or less, and even more preferably 3 nm or more and 7 nm or less.

The value of the pore mode diameter Dd is measured by a method described in the examples to be described below.

A method for adjusting the pore mode diameter Dd is not particularly limited, and the pore mode diameter Dd can be adjusted to the above range, for example, by adopting a preferable production method described below.

The half-width Wd and the pore mode diameter Dd preferably satisfy a relationship of the following expression (2):

$$\tfrac{1}{2}Wd < Dd \qquad (2)$$

In the present embodiment, the catalyst particles comprise at least one element selected from the group consisting of nickel, cobalt, palladium, lead, platinum, ruthenium, gold, silver, and copper. The catalyst particles have a function of catalyzing a reaction for producing carboxylic acid ester. The catalyst particles according to the present embodiment preferably comprise at least one element selected from the group consisting of nickel, cobalt, palladium, lead, and gold and are more preferably composite particles comprising: oxidized nickel and/or cobalt, and X, wherein X represents at least one element selected from the group consisting of nickel, palladium, platinum, ruthenium, gold, silver, and copper.

In the present embodiment, the catalyst for production of carboxylic acid ester preferably has a supported layer in which the composite particles are localized. The term "supported layer in which the composite particles are localized" refers to a region in the support where composite particles are concentratedly supported. In the catalyst for production of carboxylic acid ester of the present embodiment, composite particles are preferably supported not randomly in the support but selectively in a certain region. This region is referred to as the "supported layer in which the composite particles are localized". In the catalyst for production of carboxylic acid ester, if the composite particles are concentrated in a certain region as compared with other portions, the region is the "supported layer in which the composite particles are localized". Thus, which region is a "supported layer in which the composite particles are localized" can be determined by X-ray microprobe analysis described below or from secondary electron reflected images obtained with a high-resolution scanning electron microscope. The supported layer in which the composite particles are localized is preferably present in a region extending from the surface of the catalyst for production of carboxylic acid ester to 40% of the equivalent diameter of the catalyst for production of carboxylic acid ester. When the supported layer in which the composite particles are localized is present in this region, the influence of the diffusion rate of the reaction material within the support is reduced, and the reaction activity tends to be improved.

The catalyst for production of carboxylic acid ester of the present embodiment can have various sizes including a substantial thickness or particle diameter on the order of μm to cm, and various shapes. Specific examples of the shape of the catalyst for production of carboxylic acid ester include, but are not limited to, various shapes such as spheres, ovals, cylinders, tablets, hollow cylinders, plates, rods, sheets, and honeycombs. The shape can be suitably changed according to the reaction form, and in a fixed bed reaction, for example, hollow cylindrical or honeycomb-shaped particles are selected due to their low pressure loss, while spherical particles are typically selected under conditions of suspension of a liquid phase slurry.

The term "equivalent diameter" referred to herein represents the diameter of spherical particles, or in the case of irregularly shaped particles, the diameter of a sphere having an equal volume as the particles or having a surface area equal to the surface area of the particles. For a method for measuring the equivalent diameter, the average particle diameter (volume-based) is measured using a laser diffraction/scattering particle size distribution measuring apparatus, and the resulting value is taken as the equivalent diameter. Alternatively, the number average particle diameter as measured with a scanning electron microscope (SEM) can also be used to represent the equivalent diameter.

The optimum range of the thickness of the supported layer in which the composite particles are localized is selected according to the thickness of the support, particle diameter, type of reaction, and reaction form. Since the "equivalent diameter of the catalyst for production of carboxylic acid ester" is usually the same as the "equivalent diameter of the support", the "equivalent diameter of the catalyst for production of carboxylic acid ester" can be determined from the equivalent diameter of the support.

For example, in the case of using a support having a large equivalent diameter of the catalyst for production of carboxylic acid ester of more than 200 μm (e.g., several mm or more), the catalyst is generally used in a liquid phase reaction having a comparatively slow reaction rate or in a vapor phase reaction. Thus, by providing a layer which supports the composite particles as an active component in the region extending from the surface of the catalyst for production of carboxylic acid ester to 40% of the equivalent diameter of the catalyst for production of carboxylic acid ester and in the region extending from the outer surface of the catalyst for production of carboxylic acid ester to 80 μm and supports no composite particles inside the catalyst for production of carboxylic acid ester, a catalyst for production of carboxylic acid ester less susceptible to the influence of the diffusion rate of the reaction material tends to be obtained. As a result, the composite particles can be effectively used.

On the other hand, when the equivalent diameter of the catalyst for production of carboxylic acid ester is 200 μm or less, the composite particles are preferably supported in the region extending from the surface of the catalyst for production of carboxylic acid ester to 30% of the equivalent diameter of the catalyst for production of carboxylic acid ester. In the case of using in a liquid phase reaction, in particular, the support has been designed to have a small particle diameter in line with the reaction because the influence of the reaction rate and the intrapore diffusion rates of reaction materials within the support occurs. In the present embodiment, reducing the thickness of the supported layer in which the composite particles are localized enables a highly active catalyst for production of carboxylic acid ester to be obtained without reducing the particle diameter of the support. In this case, separation of the catalyst by settling is facilitated, and additionally, the catalyst can be advantageously separated using a small-volume separator. Meanwhile, if the volume of the portion in which composite particles in the catalyst for production of carboxylic acid ester are not supported becomes excessively large, the volume not required by the reaction per reactor increases, thereby resulting in waste in some cases. Accordingly, it is preferable to set the particle diameter of the support according to the reaction form and to set the required thickness of the supported layer in which the composite particles are localized and the thickness of the layer in which composite particles are not supported.

The catalyst for production of carboxylic acid ester may also have an outer layer substantially free of composite particles on the outside of the supported layer in which the composite particles are localized. The outer layer is preferably formed at a thickness of from 0.01 to 15 μm from the outer surface of the support. Providing the outer layer within this range enables the catalyst to be used as a catalyst that is strongly resistant to catalyst poisoning and from which falling-off of composite particles due to abrasion is suppressed, in reactions using a reactor such as a fluidized bed, bubble column, stirring reactor, or any other reactor for which friction of catalyst particles is of concern, and in reactions in which there occurs accumulation of poisoning substances. In addition, the outer layer can be controlled to be extremely thin, and thus large decrease in activity can be suppressed.

The optimum range of the thickness of the outer layer substantially free of composite particles is selected according to the reaction characteristics, physical properties of the support, amount of composite particles supported, and the like, and is preferably from 0.01 to 15 μm, more preferably from 0.1 to 10 μm, and even more preferably from 0.2 to 5 μm. If the thickness of the outer layer (composite particle-non-supported layer) is more than 15 μm, the catalyst activity may be reduced, though the effect of improving the life of the catalyst is not changed in use of the composite particles as a catalyst. If the thickness of the outer layer is less than 0.01 μm, falling-off of composite particles due to abrasion tends to easily occur.

In the present embodiment, the term "substantially free of composite particles" means the substantial absence of a peak indicating the distribution of oxidized nickel and/or cobalt and X (wherein X represents at least one of elements selected from the group consisting of nickel, palladium, platinum, ruthenium, gold, silver, and copper) having a relative intensity of 10% or more in X-ray microprobe analysis described below or in secondary electron reflected images obtained with a high-resolution scanning electron microscope.

The composite particles of the present embodiment preferably comprise oxidized nickel and/or cobalt, as described above.

Preferable examples of the oxidized nickel include nickel oxides formed by bonding nickel and oxygen (e.g., $Ni_2O$, $NiO$, $NiO_2$, $Ni_3O_4$, or $Ni_2O_3$), or composite oxides containing nickel such as nickel oxide compounds formed by bonding nickel and X and/or one or more other metal elements and oxygen, or a solid solution or mixture thereof.

Preferable examples of the oxidized cobalt include cobalt oxides formed by bonding cobalt and oxygen (e.g., $CoO$, $Co_2O_3$, or $Co_3O_4$), or composite oxides containing cobalt such as cobalt oxide compounds formed by bonding cobalt and X and/or one or more other metal elements and oxygen, or a solid solution or mixture thereof.

The term "nickel oxide" referred to herein represents a compound containing nickel and oxygen. Nickel oxides include the previously exemplified $Ni_2O$, $NiO$, $NiO_2$, $Ni_3O_4$, $Ni_2O_3$, or hydrates thereof, hydroperoxides of nickel containing an OOH group, peroxides of nickel containing an 02 group, and mixtures thereof.

The term "composite oxide" referred to herein represents an oxide containing two or more metals. The "composite oxide" refers to an oxide in which two or more metal oxides form a compound. Although including multiple oxides not containing an ion of an oxoacid as a structural unit (e.g., perovskite oxides and spinel oxides of nickel), the composite oxide has a broader concept than that of multiple oxides, including all oxides in which two or more metals are compounded. Oxides in which two or more metal oxides form a solid solution are also within the scope of composite oxides.

In the catalyst for production of carboxylic acid ester of the present embodiment, on compounding nickel oxide and/or cobalt oxide with X as described above, the inherent catalytic ability of nickel oxide and/or cobalt oxide having oxidative esterification activity can be brought out, and a markedly high level of catalyst performance, which cannot be achieved with a catalyst composed of each component singly, tends to appear. This is thought to be because a unique effect developed by compounding nickel oxide and/or cobalt oxide and X, that is, a novel catalyst action completely different from that of each component singly, is generated by a dual functional effect between both the metal components, the formation of a new active species, or the like. Further, in the case of supporting oxidized nickel and/or oxidized cobalt and X on a support in a highly dispersed state, revolutionary catalyst performance unable to be obtained with conventional catalysts tends to be achieved.

For example, if gold is selected for X and nickel oxide and gold are supported on a support in a highly dispersed state, markedly high catalyst performance tends to appear. Such a catalyst for production of carboxylic acid ester has higher selectivity for carboxylic acid ester, in comparison with a catalyst in which each of nickel oxide or gold is supported singly on the support, and tends to exhibit improved activity when the compositional ratio of Ni/Au is within a specific range. The catalyst also exhibits high catalytic activity per metal atom as compared with a particle supported material composed of each component singly, and development of catalyst performance caused by the compounding is strongly dependent on the composition of nickel and gold supported. This is presumed to be due to the presence of an optimum ratio for formation of a nickel oxidation state that is optimum for the reaction. Since the two components: the nickel oxide and gold are dispersed and supported on a support in this manner, highly outstanding compounding effects, which cannot be predicted from the simple combined addition of each component singly, tends to be developed.

The catalyst for production of carboxylic acid ester in which gold is selected for X has the oxidized nickel and gold supported on a support in a highly dispersed state, and both the components tend to be compounded at the nano-size level. When such a catalyst for production of carboxylic acid ester is observed with a transmission electron microscope/ scanning transmission electron microscope (TEM/STEM), typically a structure is observed in which nearly spherical nanoparticles of 2 to 3 nm are uniformly dispersed and supported on a support.

When the catalyst is subjected to an elementary analysis of the nanoparticles by energy dispersive X-ray spectrometry (EDS), typically, the catalyst is observed to be in a form in which nickel and gold coexist in all the particles and the surface of gold nanoparticles is coated with nickel, and also a nickel component is observed to be singly supported on the support in addition to the nanoparticles containing nickel and gold.

Further, subjecting the catalyst to X-ray photoelectron spectroscopy (XPS) and powder X-ray diffraction (powder XRD) enables the state of existence of the metals to be confirmed. Typically, while gold is observed to exist as a crystalline metal, nickel is observed to exist as an amorphous oxide having a valence of 2.

Further, when the catalyst is subjected to ultraviolet-visible spectroscopy (UV-Vis), with which change in the excited state of electrons can be observed, typically, a surface plasmon absorption peak (at about 530 nm) originating from gold nanoparticles observed in gold nanoparticles of a single metal species is observed to disappear due to compounding of nickel oxide and gold. The phenomenon of disappearance of this surface plasmon absorption peak has not been observed in catalysts composed of combinations of gold and metal oxide species other than nickel oxide not observed to have any effect on the reaction (e.g., metal oxides such as chromium oxide, manganese oxide, iron oxide, cobalt oxide, copper oxide, and zinc oxide). The disappearance of this surface plasmon absorption peak is thought to be caused by the result of the formation of a mixed electron state via the contact interface between oxidized nickel and gold, that is, hybridization of two metallic chemical species.

Conversion to highly oxidized nickel oxide can be confirmed via color change of the catalyst and ultraviolet-visible spectroscopy (UV-Vis). As a result of adding gold to nickel oxide, the nickel oxide changes in color from grayish green to brown, and the UV spectrum demonstrates absorbance over nearly the entire visible light region. The shape of the UV spectrum and the color of the catalyst are similar to those of a highly oxidized nickel oxide ($NiO_2$) measured as a reference sample. As described above, the nickel oxide is presumed to be converted to a highly oxidized nickel oxide due to the addition of gold.

From the above results, the structure of the composite particles in the case of selecting gold for X is believed to be in a form in which the gold particles serve as the core and the surface thereof is coated with a highly oxidized nickel oxide, without any gold atoms present on the surface of the composite particles.

The composite particles are preferably supported on the support in a highly dispersed state. The composite particles are more preferably dispersed and supported in the form of microparticles or a thin film, and the average particle diameter thereof is preferably from 2 to 10 nm, more preferably from 2 to 8 nm, and even more preferably from 2 to 6 nm.

When the average particle diameter of the composite particles is within the above ranges, a specific active species structure composed of nickel and/or cobalt and X is formed, and the reaction activity tends to improve. Here, the average particle diameter in the present embodiment means the number average particle diameter as measured with a transmission electron microscope (TEM). Specifically, in an image observed with a transmission electron microscope, an area of black contrast indicates composite particles. The diameter of each of all the particles is measured, and the number average thereof can be calculated therefrom.

The composition between nickel or cobalt and X in the composite particles is preferably in a range of from 0.1 to 10, more preferably from 0.2 to 8.0, and even more preferably from 0.3 to 6.0 as a Ni/X atomic ratio or a Co/X atomic ratio. When the Ni/X atomic ratio or the Co/X atomic ratio is within the above range, a specific active species structure composed of nickel and/or cobalt and X, and oxidized nickel and/or cobalt optimal for reaction are formed. As a result, the activity and the selectivity tend to be higher than those when the atomic ratio falls outside the above range.

The form of the composite particles is not particularly limited. Preferable is a form that includes both of the components of nickel and/or cobalt and X preferably coexisting in the particles and has a phase structure, that is, any one of structures such as a solid solution structure in which chemical species randomly occupy crystal sites, a core-shell structure in which each chemical species is separated in the shape of concentric spheres, an anisotropic phase separation structure in which phases are separated anisotropically, or a heterobondphilic structure in which both chemical species are present adjacent to each other on the particle surface. More preferable is a form in which the particles have a core composed of X and the surface of the cores is coated with oxidized nickel and/or cobalt. The shape of the composite particles is not particularly limited as long as both the components are contained therein, and may take any shape such as spherical, hemispherical, or the like.

As described above, transmission electron microscopy/ scanning transmission electron microscopy (TEM/STEM), for example, is effective as an analysis technique for observing the form of the composite particles. Elementary analyses within the particles and visualization of images of the distribution of elements therein are enabled by irradiating nanoparticles observed by TEM/STEM with an electron beam. The composite particles of the present embodiment contain nickel and/or cobalt and X in all of the particles as will be indicated in the examples to be described below, and have been confirmed to have a form in which the surface of X is coated with nickel and/or cobalt. In the case in which the particles have such a form, the atomic ratio of nickel and/or cobalt to X varies according to the locations of the composition analysis points in the particles, and nickel and/or cobalt is detected in larger amounts on the edges of the particles than in the central portion thereof. Thus, the atomic ratio of nickel or cobalt to X may vary depending on the locations of the analysis points even among individual particles, and the range thereof is included in the range of the Ni/X atomic ratio or the Co/X atomic ratio as described above.

In the case in which gold, silver, or copper is selected for X, ultraviolet-visible spectroscopy (UV-Vis) is an effective means of identifying the structure thereof. In the case of nanoparticles of gold, silver, or copper singly, the photoelectric field in the visible to near infrared region is coupled with free electrons on the surface of the metal, indicating surface plasmon absorption. For example, when a catalyst including gold particles supported is irradiated with visible light, an absorption spectrum is observed that is based on plasmon resonance originating from gold particles at a wavelength of about 530 nm. However, in the catalyst for production of carboxylic acid ester including nickel oxide and gold supported according to the present embodiment, since the surface plasmon absorption thereof disappears, gold can be considered not to be present on the surface of the composite particles of the present embodiment.

The solid form of the nickel is not particularly limited as long as the predetermined activity is obtained, and preferred is an amorphous form having no diffraction peak observed in X-ray diffraction. With such a form, in use as a catalyst for an oxidation reaction, interaction with oxygen is presumed to increase. Additionally, the bonding interface between the oxidized nickel and X increases, and thus better activity tends to be obtained.

In the present embodiment, X is at least one element selected from the group consisting of nickel, palladium, platinum, ruthenium, gold, silver, and copper, and X is preferably at least one element selected from nickel, palladium, ruthenium, gold, and silver, more preferably at least one element selected from palladium and gold, and even more preferably gold.

The chemical state of X may be a metal, an oxide, a hydroxide, a composite compound containing X and nickel, cobalt, or one or more another metal elements, or a mixture thereof, and a preferable chemical state is a metal or oxide and more preferably a metal. The solid form of X is not particularly limited as long as the predetermined activity can be obtained, and the form may be either a crystalline form or an amorphous form.

The term "another metal element" herein refers to a third component element or a metal component such as an alkali metal, an alkaline earth metal, or a rare earth metal to be contained in the catalyst for production of carboxylic acid ester, besides a constituent element of the support to be described below, oxidized nickel and/or cobalt and X.

In the present embodiment, the composite particles preferably comprise oxidized nickel and gold from the viewpoint of more improving pH swing resistance. The compositional ratio between nickel and gold in the composite particles is preferably 1.1 or more and 10 or less, more preferably 2 or more and 9 or less, even more preferably 3 or more and 8 or less as a Ni/Au atomic ratio.

The catalyst for production of carboxylic acid ester of the present embodiment has oxidized nickel and/or cobalt and X supported on a support as described above, and exerts excellent effects as a result of forming composite particles composed of oxidized nickel and/or cobalt and X. The term "composite particle" herein refers to a particle containing different binary metal species in a single particle. Examples of binary metal species different from this include binary metal particles in which both nickel and/or cobalt and X are metals and metal particles forming an alloy or intermetallic compound of nickel and/or cobalt and X. In the case of using these as catalysts for chemical synthesis, the selectivity of the target product and the catalyst activity tend to be lower as compared with the catalyst for production of carboxylic acid ester of the present embodiment.

The catalyst for production of carboxylic acid ester of the present embodiment preferably contains oxidized nickel and/or cobalt singly on the support in addition to the composite particles composed of oxidized nickel and/or cobalt and X. The presence of oxidized nickel and/or cobalt not compounded with X further enhances the structural stability of the catalyst for production of carboxylic acid ester and inhibits increase in the pore diameter caused by a prolonged reaction as well as the accompanying growth of the composite particles. This effect tends to become marked in the case of using an aluminum-containing silica-based composition containing silica and alumina as the support, as will be described below.

Hereinafter, there will be described action that enhances the structural stability of the catalyst for production of carboxylic acid ester and that inhibits increase in the pore diameter caused by a prolonged reaction as well as the accompanying growth of composite particles by allowing oxidized nickel and/or cobalt singly to be present on the support.

As will be described below, in a synthesis reaction of carboxylic acid ester, by-production of acetal or the like caused by acidic substances exemplified by methacrylic acid or acrylic acid, which is a by-product unique to the production reaction of carboxylic acid ester, tends to be inhibited by adding a compound of an alkali metal or alkaline earth metal to the reaction system to maintain the pH of the reaction system at 6 to 9, and more preferably at neutral conditions (e.g., pH 6.5 to 7.5), that is, as close to pH 7 as possible.

According to studies conducted by the present inventors, in the case of carrying out a prolonged reaction according to the reaction procedure using a gold particle supported material in which single-component gold particles are supported on a support composed of an aluminum-containing silica-based composition containing silica and alumina, structural changes tend to occur, although gradually, in the gold particle supported material. This phenomenon is thought to be caused by increase in the pore diameter of the supported material particles, which increase is brought about because the supported material particles are locally and repeatedly exposed to acid and base by the reaction procedure, and thus a portion of the Al in the support dissolves and precipitates, resulting in rearrangement of the silica-alumina crosslinked structure. In addition, accompanying the change of increase in the pore diameter, sintering of the gold particles occurs to cause the surface area to be decreased, and thus the catalyst activity tends to decrease.

On the other hand, the presence of composite particles and oxidized nickel and/or cobalt singly on the support enhances the structural stability of the supported material particles according to the reaction procedure described above, and increase in the pore diameter and growth of the composite particles tend to be inhibited. As described above, the formation of a nickel and/or cobalt oxide compound or a composite oxide containing nickel and/or cobalt in the form of a solid solution and the like due to reaction of oxidized nickel and/or cobalt with constituent elements of the support is considered to be a factor behind the reason. As a result of action of such a nickel compound on stabilization of the silica-alumina crosslinked structure, structural change in the supported material particles is thought to have greatly improved. The present inventors have presumed that the appearance of the structural stabilizing effect of this supported material is attributable to the oxidized nickel and/or cobalt present in the support. For this reason, this effect is naturally obtained when oxidized nickel and/or cobalt contained in composite particles is in contact with the support, and an even greater stabilizing effect is thought to be obtained when oxidized nickel and/or cobalt is present singly on the support.

The support of the catalyst for production of carboxylic acid ester of the present embodiment is not particularly limited as long as the support can support the catalyst particles according to the present embodiment, and conventional catalyst supports used for chemical synthesis can be used.

Examples of supports include various types of supports such as activated carbon, silica, alumina, silica-alumina, titania, silica-titania, zirconia, magnesia, silica-magnesia, silica-alumina-magnesia, calcium carbonate, zinc oxide, zeolite, and crystalline metallosilicate. Preferable examples of supports include activated carbon, silica, alumina, silica-alumina, silica-magnesia, silica-alumina-magnesia, titania, silica-titania, and zirconia, and more preferable examples include silica-alumina and silica-alumina-magnesia.

The support may contain one or more metal components selected from alkali metals (Li, Na, K, Rb, and Cs), alkaline earth metals (Be, Mg, Ca, Sr, and Ba), and rare earth metals (La, Ce, and Pr). Metal components to be supported on the support are preferably metal components that become oxides by firing or the like, such as nitrates or acetates.

A support composed of an aluminum-containing silica-based composition containing silica and aluminum is preferably used for the support. In other words, the support preferably contains silica and alumina. The support has higher water resistance than that of silica and higher acid resistance than that of alumina. The support comprises characteristics superior to those of conventional supports typically used, including greater hardness and higher mechanical strength than those of activated carbon, and is also able to stably support the active components: oxidized nickel and/or cobalt and X. Consequently, the catalyst for production of carboxylic acid ester tends to maintain high reactivity over a longer period.

The catalyst for production of carboxylic acid ester having a specific atomic ratio for oxidized nickel and/or cobalt and X and including an aluminum-containing silica-based composition for the support, when used as a catalyst for chemical synthesis, tends to have high mechanical strength, be physically stable, and satisfy corrosion resistance with respect to liquid properties unique to the reaction while having a large surface area suitable for use as a catalyst support.

Hereinafter, there will be described the characteristics of a support composed of an alumina-containing silica-based composition containing silica and alumina of the present embodiment, which has enabled the catalyst life to be considerably improved. Reasons why the mechanical strength and chemical stability of the support have been able to be greatly improved are presumed as follows.

In the support composed of an aluminum-containing silica-based composition, addition of aluminum (Al) to an uncrosslinked silica (Si—O) chain of a silica gel leads to new formation of Si—O—Al—O—Si bonds, and it is considered that the formation of an Al-crosslinked structure without any loss of the inherent stability to acidic substances of the Si—O chain has allowed the Si—O bonds to be strengthened and the stability of hydrolysis resistance (hereinafter, simply referred to as "water resistance") to be considerably improved. When a Si—O—Al—O—Si cross-linked structure is formed, the number of uncrosslinked Si—O chains decreases in comparison with the case of silica gel singly, and also the mechanical strength is thought to increase. That is, the number of Si—O—Al—O—Si structures formed and improvement of the mechanical strength and water resistance of the resulting silica gel is presumed to be correlated.

One of the reasons why the oxidized nickel and/or cobalt and X can be stably supported on a support for a long period is that the support has greatly improved mechanical strength and chemical stability, as described above, and comprises superior physical properties in comparison with typically used conventional supports. As a result, it is considered that nickel and/or cobalt and X, the active components, are unlikely to be separated from the support and can be stably supported over a long period.

In a commonly used support such as silica or silica-titania, nickel and/or cobalt components tend to elute from the support, although gradually, in prolonged reactions. In contrast, when the support described above is used, elution of nickel and/or cobalt components tends to be suppressed over a long period. Particularly, on the basis of the results of X-ray photoelectron spectroscopy (XPS), transmission electron microscopy (TEM/EDX), and a double crystal high-resolution X-ray fluorescence method (HRXRF), when a silica or silica-titania support is used, eluted nickel and/or cobalt components have been confirmed to be nickel oxide or cobalt oxide present singly on the support. Since nickel oxide or cobalt oxide is a compound soluble in acid, when used for a catalyst for carboxylic acid ester synthesis, the oxide is presumed to be eluted by an acidic substance typified by methacrylic acid or acrylic acid that are unique by-products of the reaction.

On the basis of analyses of the chemical state of nickel and/or cobalt by a double crystal high-resolution X-ray fluorescence method (HRXRF), as for the nickel and/or cobalt in the catalyst for production of carboxylic acid ester of the present embodiment, it is presumed that there has been formed not only nickel oxide and/or cobalt oxide as a single compound but also a composite oxide containing nickel and/or cobalt such an oxidized compound of nickel and/or cobalt formed as a result of bonding between nickel oxide and/or cobalt oxide and constituent component elements of the support, or a solid solution or mixture thereof.

The double crystal high-resolution X-ray fluorescence method (HRXRF) has extremely high energy resolution and is able to analyze a chemical state from the energy levels (chemical shifts) and shapes of the resulting spectrum. In the $K\alpha$ spectra of 3d transition metal elements in particular, changes appear in the chemical shift and shape due to changes in the valence or electronic state, thereby making it possible analyze the chemical state in detail. In the catalyst for production of carboxylic acid ester of the present embodiment, changes typically appear in the $NiK\alpha$ spectrum, as in the examples to be described below, and a chemical state is confirmed for nickel that differs from that of nickel oxide as a single compound.

For example, nickel aluminate, which is formed from nickel oxide and alumina, is a compound insoluble in acid. As a result of forming such a nickel compound on a support, elution of the nickel component is presumed to have been greatly improved.

In the present embodiment, the support is preferably a silica-based material containing silicon, aluminum, at least one period 4 element selected from the group consisting of iron, cobalt, nickel, and zinc, and at least one basic element selected from the group consisting of an alkali metal element, an alkaline earth metal element, and a rare earth element, wherein contents thereof are in ranges of 42 mol % or more and 90 mol % or less, 3 mol % or more and 38 mol % or less, 0.5 mol % or more and 20 mol % or less, and 2 mol % or more and 38 mol % or less, respectively, based on the total molar amount of the silicon, the aluminum, the period 4 element, and the basic element.

When the silica-based material containing silicon, aluminum, the period 4 element, and the basic element contains 42 to 90 mol % of silicon, 3 to 38 mol % of aluminum, 0.5 to 20 mol % of the period 4 element, and 2 to 38 mol % of the basic element, based on the total molar amount of the silicon, the aluminum, the period 4 element, and the basic element, the silicon, the aluminum, the period 4 element, the basic element, and an oxygen atom form a specific stable bonding structure with each other. Furthermore, the bonding structure is easily formed in a state uniformly dispersed in the silica-based material. From the above viewpoints, in the present embodiment, it is more preferable to contain 70 to 90 mol % of silicon, 5 to 30 mol % of aluminum, 0.75 to 15 mol % of the period 4 element, and 2 to 30 mol % of the basic element, and it is even more preferable to contain 75 to 90 mol % of silicon, 5 to 15 mol % of aluminum, 1 to 10 mol % of the period 4 element, and 2 to 15 mol % of the basic element. Particularly, when the compositional ratio of the period 4 element is 0.75 mol % or more and these components are uniformly dispersed in the whole material, the structure has few portions in which the period 4 element is absent and the resulting silica-based material tends to exhibit resistance (high acid resistance and base resistance) even when repetitively exposed to an acid and/or a base. From the viewpoint of obtaining a silica-based material having high mechanical strength and a large specific surface area, the content of the period 4 element is preferably 10 mol % or less, and the content of the basic element is preferably 30 mol % or less.

The compositional ratio between silicon and aluminum is set to a range preferable from the viewpoint of the acid resistance, base resistance, and water resistance of the silica-based material. The compositional ratio of silicon to aluminum is preferably (silicon/aluminum)=2 to 4. If the (silicon/aluminum) ratio is smaller than the above range, the acid resistance and the base resistance tend to be reduced. If the (silicon/aluminum) ratio is larger than the above range, the water resistance tends to be reduced.

Examples of alkali metals of the basic metal components include Li, Na, K, Rb, and Cs, examples of alkaline earth metals include Be, Mg, Ca, Sr and Ba, and examples of rare earth metals include La, Ce, and Pr.

For example, when nickel and magnesium are selected as the period 4 element and the basic element, respectively, and a silica-based material composed of a composite oxide containing silicon-aluminum-nickel-magnesium is analyzed for the chemical state of nickel by a double crystal high-resolution X-ray fluorescence method (HRXRF), the nickel in the silica-based material of the present embodiment is not present as nickel oxide as a single compound. The nickel is present as a composite oxide containing nickel such an oxidized compound of nickel formed as a result of bonding between nickel oxide and alumina and/or magnesia, or a solid solution or mixture thereof.

In the silica-based material described above, it is presumed that nickel is present as, for example, nickel aluminate $(NiAl_2O_4)$ which is a spinel compound of nickel oxide and alumina, or a solid solution $(NiOMgO)$ of nickel oxide and magnesia. As for the period 4 element other than nickel, it is considered that an oxide thereof forms a spinel compound with alumina or a solid solution with a basic metal oxide and thereby acts on stabilization of a silica-alumina crosslinked structure, enhancing chemical stability.

When the period 4 element is nickel and the basic element is magnesium, the silica-based material composed of a composite oxide containing silicon, aluminum, nickel, and magnesium preferably contains 42 to 90 mol % of silicon, 3 to 38 mol % of aluminum, 0.5 to 20 mol % of nickel, and 2 to 38 mol % of magnesium, based on the total molar amount of the silicon, the aluminum, the nickel, and the magnesium, from the viewpoint of acid resistance, base resistance, mechanical strength, and water resistance. The silica-based material more preferably contains 70 to 90 mol % of silicon, 5 to 30 mol % of aluminum, 0.75 to 15 mol % of nickel, and 2 to 30 mol % of magnesium, and even more preferably 75 to 90 mol % of silicon, 5 to 15 mol % of aluminum, 1 to 10 mol % of nickel, and 2 to 15 mol % of magnesium. When the elementary composition of silicon, aluminum, nickel, and magnesium is within the above ranges, the silicon, the aluminum, the nickel, and the magnesium easily form a specific stable bonding structure. Particularly, in the case of a more preferable compositional ratio, it is expected that the above stable bonding structure, when supposed to be uniformly dispersed in the silica-based material, is formed at an existing density sufficient for contributing to stabilization of the whole silica-based material. As a result, the silica-based material tends to exhibit satisfactory acid resistance, base resistance, and mechanical strength capable of meeting repetitive use.

[Determination of Contents of Constituent Elements of Silica-Based Material and Noble Metal Supported Material]

The concentrations of Si, Al, the period 4 element, and the basic element in the silica-based material described above are quantified using an ICP emission analyzer (ICP-AES, MS), "IRIS Intrepid II Model XDL" (trade name) manufactured by Thermo Fisher Scientific K.K. Samples are prepared as described below.

First, a silica-based material is weighed into a Teflon® decomposition vessel, and nitric acid and hydrogen fluoride are added thereto. The resulting solution is heated and decomposed in a microwave decomposer, "ETHOS Model TC" (trade name) manufactured by Milestone General followed by evaporating to dryness over a heater. Then, nitric acid and hydrochloric acid are added to the precipitated residue, and the mixture is decomposed under applied pressure in the microwave decomposer. Pure water is added to the resulting decomposition liquid to make a predetermined volume, and this solution is used as the sample.

Quantification of the samples is carried out by an internal standard method in the ICP-AES. The contents of Si, Al, the period 4 element, and the basic element in the silica-based material and the contents of metal elements in the noble metal supported material are determined by subtracting a simultaneously determined operation blank value, and the compositional ratio (mole-based) and the amount supported are calculated.

Next, a preferable method for preparing a support having a structure or a composition as described above will be described.

The method for preparing a support composed of an aluminum-containing silica-based composition containing silica and alumina is not particularly limited. For example, the support can be prepared by subjecting an aluminum-containing silica composition obtained through the reaction between a silica sol and an aluminum compound solution to hydrothermal synthesis under conditions described below followed by drying and firing.

Hereinafter, the support preparation methods will be described in detail.

For example, a silica sol or silica gel is used for the silica source. The silica gel is only required to have uncrosslinked Si sites that react with Al, and the length of the Si—O chain is not particularly restricted. The aluminum compound is preferably a water-soluble compound such as sodium aluminate, aluminum chloride hexahydrate, aluminum perchlorate hexahydrate, aluminum sulfate, aluminum nitrate nonahydrate, or aluminum diacetate, but a compound insoluble in water, such as aluminum hydroxide or aluminum oxide, can also be used as long as being a compound that reacts with uncrosslinked Si in the silica sol and silica gel.

After obtaining a mixed sol containing a silica sol and an aluminum compound by mixing the silica sol and the aluminum compound, the mixed sol is subjected to a multi-stage hydrothermal reaction at 20 to 100° C. for 1 to 48 hours and dried to obtain a gel followed by firing under temperature, time and atmospheric conditions described below. Alternatively, an alkaline aqueous solution is added to the above mixed sol followed by co-precipitating the silica and an aluminum compound, carrying out hydrothermal synthesis under conditions described below, drying, and firing. It is also possible to obtain a support composed of an aluminum-containing silica-based composition having a desired particle diameter by a step such as a step of micronizing the above mixed sol directly using a spray dryer, a step of drying the mixed sol followed by granulating the gel, or the like.

In a method for preparing a support containing silica, alumina, and an oxide of at least one of basic metals including alkali metals, alkaline earth metals, and rare earth metals, in accordance with the above method for preparing a support composed of an aluminum-containing silica-based composition containing silica and alumina, the support can be prepared by drying a slurry obtained by mixing an alkali metal oxide, alkaline earth metal oxide and/or rare earth metal oxide into silica and aluminum components, and further firing the dried slurry under conditions described below.

A common commercially available compound can be used as a raw material of the alkali metal, alkaline earth metal, or rare earth metal in the same manner as the aluminum raw material. The raw material is preferably a water-soluble compound and more preferably a hydroxide, carbonate, nitrate, or acetate.

Another preparation method that can be used is a method in which a basic metal component selected from the group consisting of alkali metals, alkaline earth metals, and rare earth metals is adsorbed onto a support composed of an aluminum-containing silica-based composition. For example, there can be applied a method using an immersion method in which a support is added to a liquid including a basic metal compound dissolved followed by drying treatment or the like, or a method using an impregnation method in which a basic compound equivalent to the pore volume is allowed to permeate into a support followed by drying treatment. However, a method in which the basic metal component is adsorbed later requires caution such as conducting liquid drying treatment under mild conditions for allowing the basic metal component to be highly dispersed in the support.

An inorganic substance or organic substance can be added to the mixed slurry of the various raw materials described above, in order to control slurry properties and finely adjust the pore structure or other characteristics of the product or the properties of the resulting support.

Specific examples of inorganic substances to be used include mineral acids such as nitric acid, hydrochloric acid, and sulfuric acid, salts of metals including alkali metals such as Li, Na, K, Rb, and Cs and alkaline earth metals such as Mg, Ca, Sr, and Ba, water-soluble compounds such as ammonia or ammonium nitrate, and clay minerals that are dispersed in water to form a suspension. Specific examples of organic substances include polymers such as polyethylene glycol, methyl cellulose, polyvinyl alcohol, polyacrylic acid, and polyacrylamide.

There are various effects of addition of inorganic substances and organic substances, and the main effects include formation of a spherical support, controlling the pore diameter and pore volume, and the like. Specifically, the liquid properties of the mixed slurry are an important factor in obtaining a spherical support. Adjusting the viscosity and solid content using an inorganic substance or inorganic substance enables the liquid properties to be altered so as to easily obtain a spherical support. The control of the pore diameter and pore volume can be carried out by a multi-stage hydrothermal synthesis step of the mixed slurry described below. It is also preferable to appropriately select and use an optimum organic compound that remains inside the support at the molding stage of the support and the residual substance of which can be removed by firing and washing operations after the molding.

In the hydrothermal synthesis step according to the present embodiment, a stirring operation of the mixed slurry is carried out while heating conditions or stirring conditions are adjusted.

As the heating conditions, it is preferable to raise the temperature to a predetermined temperature and maintain it for a predetermined time at the first stage, to decrease the temperature to a predetermined temperature and maintain it for a predetermined time at the second stage, and to raise the temperature to a predetermined temperature and maintain it for a predetermined time at the third stage. Specifically, temperature T1 at the first stage is preferably adjusted to 70 to 90° C. and maintained for 1 to 10 hours. Temperature T2 at the second stage is preferably adjusted to 20 to 40° C. and maintained for 0.5 to 10 hours. Temperature T3 at the third stage is preferably adjusted to 40 to 60° C. and maintained for 1 to 20 hours. By adopting such conditions, formation of secondary particles in the mixed slurry is easily controlled, and a pore structure that is uniform from near the inlets of pores to the inside of the pores tends to be obtained. From similar viewpoints, the value of T1−T2 is preferably from 30 to 70° C., and more preferably from 40 to 60° C., and the value of T3−T2 is preferably from 5 to 40° C., and more preferably from 15 to 30° C.

As the stirring conditions, it is preferable to adjust the tip speed of a stirring blade (hereinafter, also referred to as "stirring tip speed"), etc. The stirring tip speed V can be defined according to the following expression:

$$V = N/60 \times \pi D \ (N: \text{rational speed rpm}, D: \text{stirring blade diameter})$$

The stirring tip speed V is not particularly limited, and is preferably from 5.0 to 20 m/s.

The stirring blade diameter is not particularly limited, and can be from 0.3 to 5 m and is preferably from 0.5 to 3 m, and more preferably from 0.5 m to 2 m.

The shape of a stirring blade is not particularly limited, and examples thereof include an anchor-type stirring blade, a paddle-type stirring blade, and a turbine-type stirring blade. From the viewpoint of shearing performance, a paddle-type stirring blade and a turbine-type stirring blade are preferable, and a turbine-type stirring blade is more preferable. Examples of the turbine-type stirring blade include a radial flow turbine blade, an axial flow turbine blade, and an edged turbine blade.

In the hydrothermal synthesis step according to the present embodiment, either of the heating conditions or the stirring conditions are preferably adopted, and both the conditions are more preferably adopted.

The support can be produced by spray-drying a mixed slurry of various raw materials described above and an additive. A known spraying apparatus such as a rotating disk type, two-fluid nozzle type, or pressurized nozzle type can be used, for a method for converting the mixed slurry into droplets.

The liquid to be sprayed is required to be used in a well-mixed state. If the liquid is in an insufficiently mixed state, the performance of the support is affected, such as decreased durability caused by uneven distribution of the composition. Particularly, on formulating the raw materials, increases in the slurry viscosity or partial gelling (colloidal condensation) may occur, resulting in a concern of formation of non-uniform particles. For this reason, in addition to taking into consideration gradually mixing the raw materials while stirring, for example, controlling the pH to a semi-stable region of the silica sol such as around pH 2 may be preferable by using a method such as adding acid or alkali.

The liquid to be sprayed needs to have certain degrees of a viscosity and a solid content. If the viscosity or the solid content is too low, a porous material obtained by spray drying forms many indentations without forming a perfect sphere. If the viscosity or the solid content is too high, in addition to having a detrimental effect on the dispersibility of porous materials, droplets cannot be stably formed depending on the properties thereof. Hence, the viscosity is preferably in a range of from 5 to 10000 cp as long as the liquid can be sprayed. In terms of the shape, higher viscosities tend to be preferable as long as the liquid can be sprayed. In consideration of the balance with ease of manipulation, the viscosity is more preferably selected from within a range of from 10 to 1000 cp. The solid content is preferably within a range of from 10 to 50% by mass in terms of the shape and particle diameter. As a measure for spray-drying conditions, the hot air temperature at the drying chamber inlet of the spray dryer is preferably from 200 to 280° C., and the temperature at the outlet of the drying chamber is preferably in a range of from 110 to 140° C.

The support firing temperature is typically selected within a range of from 200 to 800° C. Firing at a temperature above 800° C. is not preferable because the specific surface area tends to decrease considerably. The firing atmosphere is not particularly limited, and firing is typically carried out in air or nitrogen. The firing time can be determined according to the specific surface area after firing, and is generally from 1 to 48 hours. For firing conditions, the porosity and other properties of the support may change, and thus selection of suitable temperature conditions and heating conditions is required. If the firing temperature is excessively low, it tends to be difficult to maintain durability for a composite oxide, while if the firing temperature is excessively high, there is the risk of causing decrease in the pore volume. The temperature rise conditions are preferably such that the temperature is raised gradually using programmed temperature rising or the like. A case of abrupt firing under high temperature conditions is not preferable because gasification and combustion of inorganic substances and organic substances becomes violent, the support is exposed to a high-temperature state beyond the setting, and this exposure may cause the support to be pulverized.

From the viewpoints of ease of supporting composite particles, reaction activity in the case of using as a catalyst, difficulty in separation, and reaction activity, the specific surface area of the support is preferably 10 $m^2$/g or more, more preferably 20 $m^2$/g or more, and even more preferably 50 $m^2$/g or more as measured by BET nitrogen adsorption. There is no particular limitations from the viewpoint of activity, but from the viewpoints of mechanical strength and water resistance, the specific surface area is preferably 700 $m^2$/g or less, more preferably 350 $m^2$/g or less, and even more preferably 300 $m^2$/g or less.

If the pore diameter is smaller than 3 nm, the separation properties of the supported metal tend to be satisfactory, but in the case of using as a catalyst in a liquid phase reaction or the like, the pore diameter is preferably 3 nm or more from the viewpoints of not making the intrapore diffusion resistance excessively great so as not to cause the diffusion process of the reaction substrate to be rate-limiting as well as of maintaining the reaction activity at a high level. On the other hand, the pore diameter is preferably 50 nm or less from the viewpoints of difficulty in cracking of the supported material and difficulty in separation of the supported metal. Thus, the pore diameter of the support is preferably from 3 to 50 nm and more preferably from 3 to 30 nm. The pore volume is required for the presence of pores supporting composite nanoparticles. However, if the pore volume increases, the strength tends to suddenly decrease. Accordingly, from the viewpoints of strength and supporting characteristics, the pore volume is preferably within a range of from 0.1 to 1.0 mL/g and more preferably within a range of from 0.1 to 0.5 mL/g. The support of the present embodiment preferably satisfies the above ranges for both the pore diameter and pore volume.

The shape of the support depends on the reaction form. For a fixed bed reaction, a hollow cylindrical or honeycomb form, which results in little pressure loss, is selected. Under conditions of a liquid phase slurry suspension, generally chosen is a spherical form for which an optimum particle diameter is selected for use in accordance with the reactivity and the separation method. For example, in the case of employing a generally simple catalyst separation process based on precipitation separation, a particle diameter to be selected is preferably from 10 to 200 μm, more preferably from 20 to 150 μm, and even more preferably from 30 to 150 μm, in consideration of the balance with reaction characteristics. In the case of a cross filter system, small particles of 0.1 to 20 μm or less are preferable because of its higher reactivity. The type and form of the support can be changed according to the purpose of use for use in a catalyst for chemical synthesis.

The amount of oxidized nickel or cobalt supported on the support is not particularly limited, and is usually from 0.01 to 20% by mass, preferably from 0.1 to 10% by mass, more preferably from 0.2 to 5% by mass, and even more preferably from 0.5 to 2% by mass, as nickel or cobalt, based on the mass of the support. The amount of X supported on the support is usually from 0.01 to 10% by mass, preferably from 0.1 to 5% by mass, more preferably from 0.2 to 2% by mass, even more preferably from 0.3 to 1.5% by mass, and particularly preferably from 0.5 to 1.0% by mass, as metal, based on the mass of the support.

Moreover, in the present embodiment, a preferable range exists for the atomic ratio between nickel and/or cobalt and the above-mentioned constituent elements of the support. In the case of using the support composed of an aluminum-containing silica-based composition containing silica and alumina in the present embodiment, the compositional ratio between nickel or cobalt and alumina in a catalyst, as the Ni/Al atomic ratio or the Co/Al atomic ratio, is preferably from 0.01 to 1.0, more preferably from 0.02 to 0.8, and even more preferably from 0.04 to 0.6. In the case of using a support containing silica, alumina, and an oxide of at least one basic metal of alkali metals, alkaline earth metals, and rare earth metals, the compositional ratio between nickel or cobalt and alumina in the supported material, as the atomic ratio of Ni/Al or the Co/Al atomic ratio, is preferably from 0.01 to 1.0, more preferably from 0.02 to 0.8, and even more preferably from 0.04 to 0.6, and the compositional ratio between nickel or cobalt and the basic metal component, as the Ni/(alkali metal+alkaline earth metal+rare earth metal) atomic ratio or the Co/(alkali metal+alkaline earth metal+ rare earth metal) atomic ratio, is preferably from 0.01 to 1.2, more preferably from 0.02 to 1.0, and even more preferably from 0.04 to 0.6.

When the atomic ratios of nickel and/or cobalt to aluminum and basic metal oxide as the support constituent elements are within the above ranges, the effects of improving elution of nickel and/or cobalt and structural changes in supported material particles tend to increase. This is thought to be because the nickel and/or cobalt, aluminum, and basic metal oxide form a specific composite oxide within the above ranges, thereby forming a stable bonding structure.

The catalyst for production of carboxylic acid ester of the present embodiment can contain a third constituent element, as an activity component, in addition to oxidized nickel and/or cobalt and X. Examples of third constituent elements that can be contained include titanium, vanadium, chromium, manganese, iron, zinc, gallium, zirconium, niobium, molybdenum, rhodium, cadmium, indium, tin, antimony, tellurium, hafnium, tantalum, tungsten, rhenium, osmium, iridium, mercury, thallium, lead, bismuth, aluminum, boron, silicon, and phosphorous. The content of these third constituent elements is preferably from 0.01 to 20% by mass and more preferably from 0.05 to 10% by mass in the supported material. At least one metal component selected from alkali metals, alkaline earth metals, and rare earth metals may also be contained in the catalyst for production of carboxylic acid ester. The content of the alkali metal, alkaline earth metal, or rare earth metal is preferably selected to be within a range of 15% by mass or less in the supported material.

These third constituent elements or alkali metal, alkaline earth metal and rare earth metal may be contained in the supported material during production or reaction of the catalyst for production of carboxylic acid ester, or a method may be used in which these are contained in the support in advance.

The specific surface area of the catalyst for production of carboxylic acid ester of the present embodiment is preferably within a range of from 20 to 350 m²/g, more preferably from 50 to 300 m²/g, and even more preferably from 100 to 250 m²/g, as measured by BET nitrogen adsorption, from the viewpoints of reaction activity and resistance to separation of active components.

The pore diameter of the catalyst for production of carboxylic acid ester is originating from the pore structure of the support. If the pore diameter is smaller than 3 nm, the separation properties of the supported metal component tend to be satisfactory. However, in the case of using as a catalyst in a liquid phase reaction or the like, the pore diameter is preferably 3 nm or more, from the viewpoints of not making the intrapore diffusion resistance excessively large so as not to cause the diffusion process of the reaction substrate to be rate-limiting as well as of maintaining the reaction activity at a high level. On the other hand, the pore diameter is preferably 50 nm or less from the viewpoints of difficulty in cracking of the supported material and difficulty in separation of the supported composite particles. Thus, the pore diameter of the catalyst for production of carboxylic acid ester is preferably from 3 to 50 nm, more preferably from 3 to 30 nm, and even more preferably from 3 to 10 nm. From the viewpoints of supporting characteristics and reaction characteristics, the pore volume is preferably within a range of from 0.1 to 1.0 mL/g, more preferably from 0.1 to 0.5 mL/g, and even more preferably from 0.1 to 0.3 mL/g. The catalyst for production of carboxylic acid ester of the present embodiment preferably satisfies the above ranges for both the pore diameter and pore volume.

[Method for Producing Catalyst for Production of Carboxylic Acid Ester]

The method for producing a catalyst for production of carboxylic acid ester of the present embodiment is not particularly limited and can include the following preferable steps. Hereinafter, each step will be described.

In a first step, an aqueous slurry containing a support is mixed with an acidic aqueous solution of soluble metal salts containing at least one element selected from the group consisting of nickel, cobalt, palladium, lead, platinum, ruthenium, gold, silver, and copper. The temperature of the mixture of both liquids is adjusted so as to be 60° C. or more. A precursor of a catalyst for production of carboxylic acid ester in which the catalyst particles have precipitated on the support is formed in the mixture.

Next, in a second step, the precursor obtained in the first step is washed with water and dried as necessary followed by subjecting to heat treatment, and thus the catalyst for production of carboxylic acid ester can be obtained.

According to this method, a catalyst for production of carboxylic acid ester can be obtained that has a supported layer in which the composite particles are localized but does not contain composite particles in a region that includes the center of the support.

In the present embodiment, prior to the first step, it is preferable to carry out a water dispersion step of dispersing the support in water for aging. Dispersing the support in water in advance allows a layer having a sharp distribution of composite particles to be obtained. The effect caused by dispersing the support in water is presumed, based on the results of measuring pore distribution by nitrogen adsorption, to be attributable to a more uniform and sharper pore structure due to occurrence of realignment of the pore structure of the support. Although the water dispersion can be carried out at room temperature, the water dispersion temperature for the support is preferably selected within a range of from 60 to 150° C., which is higher than room temperature, because the pore structure changes slowly. In the case in which the water dispersion is carried out at normal pressure, a temperature within a range of from 60 to 100° C. is preferable. The duration of addition of the support in adding the support to water is not particularly limited, and can be from 0.5 to 10 minutes. From the viewpoint of a smaller value of the half-width Wd, the duration is preferably from 0.5 to 8 minutes, and even more preferably from 0.5 to 6 minutes. The duration of the water dispersion varies according to the temperature conditions. In the case of 90° C., for example, the duration is preferably from 1 minute to 5 hours, more preferably from 1 to 60 minutes, and even more preferably from 1 to 30 minutes. In the operation of the first step, although the support can be used after dispersed in water, then once dried, and fired, a slurry obtained by dispersing the support in water is preferably brought into contact with the acidic aqueous solution of soluble metal salts containing at least one element selected from the group consisting of nickel, cobalt, palladium, lead, platinum, ruthenium, gold, silver, and copper followed by insoluble immobilization of the catalyst particles on the support.

Examples of soluble metal salts containing nickel include nickel nitrate, nickel acetate, and nickel chloride. Examples of soluble metal salts containing X include palladium chloride and palladium acetate in the case of selecting palladium for X, ruthenium chloride and ruthenium nitrate in the case of selecting ruthenium for X, chloroauric acid, sodium tetrachloroaurate, potassium dicyanoaurate, gold diethylamine trichloride, and gold cyanide in the case of selecting gold for X, and silver chloride and silver nitrate in the case of selecting silver for X.

The concentration of each of the aqueous solutions containing nickel and/or cobalt and X are usually within a range of from 0.0001 to 1.0 mol/L, preferably from 0.001 to 0.5 mol/L, and more preferably from 0.005 to 0.2 mol/L. The ratio of nickel or cobalt to X in the aqueous solutions, as the Ni/X atomic ratio or the Co/X atomic ratio, is preferably within a range of from 0.1 to 10, more preferably from 0.2 to 5.0, and even more preferably from 0.5 to 3.0.

The temperature during contact between the support and the acidic aqueous solution is one important factor for controlling the distribution of catalyst particles, and varies according to the amount of the catalyst particles supported in advance on the support. If the temperature is excessively low, the reaction slows, and the distribution of the catalyst particles tends to widen. In the production method of the present embodiment, from the viewpoint of obtaining a supported layer in which the catalyst particles are more sharply localized, the temperature during contact with the acidic aqueous solution is a temperature at which a high reaction rate is achieved, and is preferably 60° C. or more, more preferably 70° C. or more, even more preferably 80° C. or more, and particularly preferably 90° C. or more. Since the acidic aqueous solution and the aqueous slurry may be mixed so that the temperature of the mixed liquid thereof is 60° C. or more, the aqueous slurry may be heated to a degree such that the mixed liquid exceeds 60° C. even after the acidic aqueous solution is added, or conversely only the acidic aqueous solution may be heated. Both the acidic aqueous solution and the aqueous slurry may also be heated to 60° C. or more.

The reaction can be carried out under applied pressure at a temperature equal to or higher than the boiling point of the solution, and usually preferably carried out at a temperature equal to or lower than the boiling point for the ease of the operation. The duration of immobilization of the nickel and/or cobalt and X components is not particularly limited, and depends on conditions such as the type of support, the amount of nickel and/or cobalt and X supported and the ratio thereof. The duration is usually within a range of from 1 minute to 5 hours, preferably from 5 minutes to 3 hours, and more preferably from 5 minutes to 1 hour.

The method for producing a catalyst for production of carboxylic acid ester of the present embodiment may be carried out, for example, on the basis of the principle of insoluble immobilization of the nickel and/or cobalt and X component by carrying out a chemical reaction between an oxide of at least one basic metal selected from the group consisting of alkali metals, alkaline earth metals, and rare earth metals supported in advance on the support and soluble metal salts containing nickel and/or cobalt and X. In order to ensure more sufficient compounding of the nickel and/or cobalt and X component, both the components are preferably immobilized simultaneously from a mixed solution containing both the components.

In the production method of the present embodiment, the aqueous slurry containing a support supporting an oxide of at least one basic metal selected from the group consisting of alkali metals, alkaline earth metals, and rare earth metals preferably contains a salt of at least one basic metal selected from the group consisting of alkali metals, alkaline earth metals, and rare earth metals.

Thus, formation of metal black of X can be inhibited, compounding of nickel and/or cobalt and X is facilitated, and the distribution of composite particles can be controlled more precisely. Such effects are presumed to be caused by controlling the rate of the chemical reaction between the basic metal oxide supported in advance on the support and the soluble metal salts containing nickel and/or cobalt and X by means of addition of a salt of at least one metal selected from the group consisting of alkali metals, alkaline earth metals and rare earth metals to the aqueous solution.

Examples of salts of at least one basic metal selected from the group consisting of alkali metals, alkaline earth metals, and rare earth metals that can be used include one or more selected from water-soluble salts of these metals such as organic acid salts, and inorganic salts including nitrates and chlorides.

The amount of the salt of at least one basic metal selected from the group consisting of alkali metals, alkaline earth metals, and rare earth metals described above varies according to the amounts and ratio of the nickel and/or cobalt and X component, and is determined according to the amount of the basic metal oxide supported in advance on the support. Usually, the amount of the salt is from 0.001 to 2 times moles and preferably from 0.005 to 1 time moles based on the amount of the nickel and/or cobalt and X component in the aqueous solution.

The aqueous slurry containing a support supporting an oxide of at least one basic metal selected from the group consisting of alkali metals, alkaline earth metals, and rare earth metals preferably contains a soluble aluminum salt. Examples of soluble aluminum salts that can be used include aluminum chloride and aluminum nitrate.

Addition of a soluble aluminum salt to the aqueous slurry can lead to formation of an outer layer substantially free of composite particles on the outside of the supported layer in which the composite particles are localized. This is also based on the principle of insoluble immobilization as described above. A soluble salt such as aluminum chloride or aluminum nitrate is used for the soluble aluminum salt. Aluminum is allowed to react on the outer surface of the support by a chemical reaction with the basic metal oxide supported in advance on the support, the reaction field for nickel and/or cobalt and X is consumed, and the basic metal oxide further inside and the nickel and/or cobalt and X are immobilized by a reaction.

The amount of the aluminum component varies according to the setting of the thickness (μm) of the layer not supporting the nickel and/or cobalt and X component thereon, and is determined according to the amount of the basic metal oxide supported in advance on the support. Usually, the amount of the aluminum component is from 0.001 to 2 times moles and preferably from 0.005 to 1 time mole based on the amount of the basic metal oxide supported in advance on the support.

Although much is still unknown about the details of the mechanism by which the nickel and/or cobalt and X component are distributed, it is presumed that the diffusion rate of the nickel and/or cobalt and X-containing soluble component in the support and the rate at which the components are insolubilized by a chemical reaction were well-balanced under the conditions of the present embodiment, thereby enabling the composite particles to be immobilized in a narrow region near the surface of the support.

In the case of forming an outer layer substantially free of composite particles on the outer surface of the support, aluminum and a basic metal component near the outer surface of the support are allowed to react with each other to lead to consumption of the basic metal component that may react with the nickel and/or cobalt and X component near the outer surface of the support, and when nickel and/or cobalt and X are subsequently supported, the reactive basic metal component near the outer surface of the support is already consumed. Accordingly, the nickel and/or cobalt and X are presumed to react with the basic metal oxide inside the support followed by being immobilized.

Next, the second step will be described.

The first precursor is washed with water and dried as necessary prior to the heat treatment of the second step. The heating temperature for the first precursor is usually from 40 to 900° C., preferably from 80 to 800° C., more preferably from 200 to 700° C., and even more preferably from 300 to 600° C.

The heat treatment is carried out in an atmosphere such as air (or atmospheric air), an oxidizing atmosphere (such as oxygen, ozone, nitrogen oxides, carbon dioxide, hydrogen peroxide, hypochlorous acid, or inorganic or organic peroxide), or an inert gas atmosphere (such as helium, argon, or nitrogen). The heating time is only required to be suitably selected according to the heating temperature and the amount of the first precursor. The heat treatment can be carried out at normal pressure, under applied pressure, or under reduced pressure.

Following the second step described above, a reduction treatment can be carried out in a reducing atmosphere (such as hydrogen, hydrazine, formalin, or formic acid) as necessary. In this case, a treatment method selected and carried out in which the oxidized nickel and/or cobalt are not completely reduced to a metallic state. The temperature and duration of the reducing treatment are suitably selected according to the type of the reducing agent, the type of X, and the amount of the catalyst.

Further, following the above-mentioned heat treatment or reducing treatment, oxidizing treatment can be carried out in air (or atmospheric air) or an oxidizing atmosphere (such as oxygen, ozone, nitrogen oxide, carbon dioxide, hydrogen peroxide, hypochlorous acid, or inorganic or organic peroxide), as necessary. The temperature and duration in this case is suitably selected according to the type of the oxidizing agent, the type of X, and the amount of the catalyst.

A third constituent element other than nickel and/or cobalt and X can be added during preparation of the supported material or under reaction conditions. The alkali metal, alkaline earth metal, or rare earth metal can also be added during catalyst preparation or to the reaction system. The raw materials for the third constituent element, alkali metal, alkaline earth metal, and rare earth metal are selected from salts of organic acids, salts of inorganic acids, hydroxides, and the like.

[Method for Producing Carboxylic Acid Ester]

The catalyst for production of carboxylic acid ester of the present embodiment can be widely used as a catalyst for chemical synthesis. For example, the catalyst can be used in reactions for forming carboxylic acid esters from aldehydes and alcohols and reactions for forming carboxylic acid esters from alcohols. In other words, the method for producing carboxylic acid ester of the present embodiment can include a reaction step of reacting (a) an aldehyde and an alcohol or of (b) one or two or more alcohols in the presence of the catalyst for production of carboxylic acid ester of the present embodiment and oxygen.

The catalyst for production of carboxylic acid ester of the present embodiment exerts excellent effects particularly when used as a catalyst for oxidization reactions. In addition to the aldehydes and alcohols used in the reaction for forming carboxylic acid ester as indicated in the examples, examples of reaction substrates used in the present embodiment include various reaction substrates such as alkanes, olefins, alcohols, ketones, aldehydes, ethers, aromatic compounds, phenols, sulfur compounds, phosphorous compounds, oxygen-containing nitrogen compounds, amines, carbon monoxide, and water. These reaction substrates can be used singly or as a mixture composed of two or more thereof. Various industrially useful oxidation products such as oxygen-containing compounds, oxidative adducts, and oxidative dehydrogenation products are obtained from these reaction substrates.

As specific reaction substrates, examples of alkanes include aliphatic alkanes such as methane, ethane, propane, n-butane, isobutane, n-pentane, n-hexane, 2-methylpentane, and 3-methylpentane, and alicyclic alkanes such as cyclopentane, cyclohexane, cycloheptane, and cyclooctane.

Examples of olefins include aliphatic olefins such as ethylene, propylene, butene, pentene, hexene, heptene, octene, decene, 3-methyl-1-butene, 2,3-dimethyl-1-butene, and allyl chloride; alicyclic olefins such as cyclopentene, cyclohexene, cycloheptene, cyclooctene, and cyclodecene; and aromatic substituted olefins such as styrene and α-methylstyrene.

Examples of alcohols include saturated and unsaturated aliphatic alcohols such as methanol, ethanol, n-propanol, isopropanol, n-butanol, s-butanol, t-butanol, n-pentanol, n-hexanol, n-heptanol, allyl alcohol, and crotyl alcohol; saturated and unsaturated alicyclic alcohols such as cyclopentanol, cyclohexanol, cycloheptanol, methylcyclohexanol, and cyclohexen-1-ol; aliphatic and alicyclic polyhydric alcohols such as ethylene glycol, propylene glycol, trimethylene glycol, 1,3-butanediol, 1,2-cyclohexanediol, and 1,4-cyclohexanediol; and aromatic alcohols such as benzyl alcohol, salicyl alcohol, and benzhydrol.

Examples of aldehydes include aliphatic saturated aldehydes such as formaldehyde, acetoaldehyde, propionaldehyde, isobutylaldehyde, and glyoxal; aliphatic α,β-unsaturated aldehydes such as acrolein, methacrolein, and crotonaldehyde; aromatic aldehydes such as benzaldehyde, tolylaldehyde, benzylaldehyde, and phthalaldehyde; and derivatives of these aldehydes.

Examples of ketones include aliphatic ketones such as acetone, methyl ethyl ketone, diethyl ketone, dipropyl ketone, and methyl propyl ketone; alicyclic ketones such as cyclopentanone, cyclohexanone, cyclooctanone, 2-methylcyclohexanone, and 2-ethylcyclohexanone; and aromatic ketones such as acetophenone, propiophenone, and benzophenone.

Examples of aromatic compounds include benzene, toluene, xylene, naphthalene, anthracene, or derivatives thereof obtained by substitution with an alkyl group, an aryl group, a halogen, a sulfone group, or the like.

Examples of phenols include phenol, cresol, xylenol, naphthol, anthrol (hydroxyanthracene), and derivatives thereof (such as those obtained by replacing a hydrogen atom in the aromatic ring with an alkyl group, an aryl group, a halogen atom, a sulfonic acid group, or the like).

Examples of sulfur compounds include mercaptans such as methyl mercaptan, ethyl mercaptan, propyl mercaptan, benzyl mercaptan, and thiophenol.

Examples of amines include aliphatic amines such as methylamine, ethylamine, propylamine, isopropylamine, butylamine, dimethylamine, diethylamine, dipropylamine, diisopropylamine, dibutylamine, trimethylamine, triethylamine, tripropylamine, tributylamine, allylamine, and diallylamine; alicyclic amines such as cyclopentylamine, cyclohexylamine, cycloheptylamine, and cyclooctylamine; and aromatic amines such as aniline, benzylamine, and toluidine.

These reaction substrates can be used singly or as a mixture composed of two or more thereof. The reaction substrates are not necessarily required to be purified, and may be in a form of mixture with other organic compounds.

Hereinafter, a method for producing carboxylic acid ester from an aldehyde and an alcohol in the presence of oxygen by an oxidative esterification reaction using the catalyst for production of carboxylic acid ester of the present embodiment will be described by way of example.

Examples of the aldehyde used as a raw material include $C_1$ to $C_{10}$ aliphatic saturated aldehydes such as formaldehyde, acetoaldehyde, propionaldehyde, isobutylaldehyde, and glyoxal; $C_3$ to $C_{10}$ alicyclic $\alpha \cdot \beta$-unsaturated aldehydes such as acrolein, methacrolein, and crotonaldehyde; $C_6$ to $C_{20}$ aromatic aldehydes such as benzaldehyde, tolylaldehyde, benzylaldehyde, and phthalaldehyde; and derivatives of these aldehydes. These aldehydes can be used singly or as a mixture of any two or more thereof. In the present embodiment, the aldehyde is preferably selected from acrolein, methacrolein, or a mixture of these.

Examples of alcohols include $C_1$ to $C_{10}$ aliphatic saturated alcohols such as methanol, ethanol, isopropanol, butanol, 2-ethylhexanol, and octanol; $C_5$ to $C_{10}$ alicyclic alcohols such as cyclopentanol and cyclohexanol; $C_2$ to $C_{10}$ diols such as ethylene glycol, propylene glycol, and butanediol; $C_3$ to $C_{10}$ aliphatic unsaturated alcohols such as allyl alcohol and methallyl alcohol; $C_6$ to $C_{20}$ aromatic alcohols such as benzyl alcohol; and hydroxyoxetanes such as 3-alkyl-3-hydroxymethyloxetane. These alcohols can be used singly or as a mixture of any two or more thereof. In the present embodiment, it is preferable that the aldehyde be acrolein and/or methacrolein and the alcohol be methanol.

In the present embodiment, from the viewpoint of further improving reaction results, the moisture content in the alcohol is preferably 10% by mass or less, more preferably 0.01% by mass or more and 10% by mass or less, more preferably 7% by mass or less, even more preferably 5% by mass or less, and still even more preferably 1% by mass or less.

A smaller moisture content in the alcohol is preferable, and thus the lower limit value is not particularly limited. For example, the moisture content may be 0.01% by mass or may be a value smaller than this value.

The amount ratio of the aldehyde to the alcohol is not particularly limited, and the reaction can be carried out over a wide range of a molar ratio of aldehyde/alcohol of from 10 to 1/1,000. The reaction is generally carried out within the range of a molar ratio of from 1/2 to 1/50.

The amount of catalyst used can be varied considerably according to the types of reaction raw materials, the composition of the catalyst, preparation method, reaction conditions and reaction form, and the like and is not particularly limited. In the case of allowing the catalyst to react in a slurry form, the amount of catalyst used, in terms of the solid content in the slurry, is preferably within the range of from 1 to 50 mass/vol %, more preferably from 3 to 30 mass/vol %, and even more preferably from 10 to 25 mass/vol %.

The production of carboxylic acid ester may be carried out as a batch or continuous process by any method such as a vapor phase reaction, liquid phase reaction, or irrigation liquid reaction, and the reaction step is preferably performed in a liquid phase.

The reaction can be carried out in the absence of solvent, and can also be carried out using a solvent that is inert to the reaction components such as hexane, decane, benzene, dioxane, or the like.

The reaction can be carried out by means of a conventionally known form, such as a fixed bed form, a fluid bed form, or a stirred tank form. For example, when carried out in the liquid phase, the reaction can be carried out by means of any form of reaction vessel, such as a bubble column reactor, a draft tube reactor, or a stirred tank reactor.

The oxygen used to produce carboxylic acid ester can be molecular oxygen, that is, can be in the form of oxygen gas itself or a mixed gas in which oxygen gas has been diluted with a diluent inert to the reaction such as nitrogen or carbon dioxide gas. Air is preferably used for the oxygen raw material from the viewpoints of ease of manipulation, economy, and the like.

The oxygen partial pressure varies according to the reaction raw materials such as the type of aldehyde or type of alcohol, the reaction conditions or the type of reactor, and the like. The oxygen partial pressure at the reactor outlet is practically within the range equal to or lower than the lower limit of the explosive range, and is preferably controlled to, for example, from 20 to 80 kPa. The reaction can be carried out at a reaction pressure within a wide pressure range from reduced pressure to applied pressure, and is usually carried out at a pressure within the range of from 0.05 to 2 MPa. From the viewpoint of safety, the total pressure is preferably set such that the oxygen concentration of the reactor outflow gas does not exceed the explosive limit (e.g., an oxygen concentration of 8%).

In the present embodiment, the reaction step is preferably performed while a basic substance is added so that pH of the reaction system is 6 or more and 8 or less. Examples of the basic substance include compounds of alkali metals or alkaline earth metals (e.g., oxides, hydroxides, carbonates, and carboxylates). These alkali metal or alkaline earth metal compounds can be used singly or in combination of two or more thereof.

The reaction can be carried out even at a high temperature of 200° C. or more, and the reaction temperature during production of carboxylic acid ester is preferably from 30 to 200° C., more preferably from 40 to 150° C., and even more preferably from 60 to 120° C. The reaction time is not particularly limited, cannot be determined unconditionally because of varying according to the set conditions, and is usually from 1 to 20 hours.

EXAMPLES

The present embodiment will be now further described with reference to the following examples, but the present embodiment is not limited to the examples.

In the following examples and comparative examples, measurement of distributions of nickel and X in a composite particle supported material, shape observation of a support and the composite particle supported material, measurement of average particle diameters, determination of the amounts of Ni and X supported and a Ni/(Ni+X) atomic ratio, determination of the contents of support component elements (Si, Al, and a basic metal), analysis of the crystal structure of composite particles, analysis of the chemical state of composite particle metal components, analysis of the chemical state of nickel, morphological observation and elementary analysis of the composite particles, measurement of ultraviolet-visible spectra of the composite particles, and measurement of the physical properties (specific surface areas, pore diameters, and pore volumes) of the support and the composite particle supported material were carried out in accordance with the following methods.

[Measurement of Distributions of Nickel and X in Composite Particle Supported Material]

Samples obtained by embedding the resulting composite particle supported material in a resin and polishing were measured at an acceleration voltage of 15 kV using model 1600 X-ray microprobe (EPMA) manufactured by Shimadzu Corp. Ni and X (Au) in the direction of depth from the outer surface were analyzed on the basis of reflected electron images and ray analysis (for Ni, wavelength: 14.5829, analyzing crystal: RAP; for X (Au), wavelength: 5.8419, analyzing crystal: PET).

[Shape Observation of Support and Composite Particle Supported Material]

The support and the composite particle supported material were observed using an X-650 scanning electron microscope (SEM) manufactured by Hitachi, Ltd.

[Measurement of Average Particle Diameters of Support and Composite Particle Supported Material]

The average particle diameters (volume-based) were measured using model LS230 laser diffraction/scattering particle size distribution measuring apparatus manufactured by Beckman Coulter Inc.

[Determination of Amounts of Ni and X Supported and Ni/X Atomic Ratio]

The concentrations of nickel and X in the composite particle supported material were quantified using model IRIS Intrepid II XDL ICP emission analyzer (ICP-AES, MS) manufactured by Thermo Fisher Scientific K.K.

For preparation of samples, the supported material was weighed into a Teflon decomposition vessel, and nitric acid and hydrogen fluoride were added thereto. The resulting solution was heated and decomposed in ETHOS Model TC microwave decomposer manufactured by Milestone General followed by evaporating to dryness over a heater. Then, nitric acid and hydrochloric acid were added to the precipitated residue, and the mixture was decomposed under applied pressure in the microwave decomposer. Pure water was added to the resulting decomposition liquid to make a predetermined volume, and this solution was used as the sample.

In a quantification method, quantification was carried out by an internal standard method in the ICP-AES. The contents of nickel and X in the catalyst were determined by subtracting a simultaneously determined operation blank value, and the amount supported and the atomic ratio were calculated.

[Determination of Contents of Support Component Elements (Si, Al, and Basic Metal)]

Samples were prepared by dissolving the support in aqua regia and in molten alkali salt. The content of the basic metal and/or Mg was measured for the sample dissolved in aqua regia and the contents of Al and Si were measured for the sample dissolved in molten alkali salt, using the model JY-38P2 ICP emission analyzer (ICP-AES) manufactured by Seiko Instruments Inc. The atomic ratios were calculated from the resulting metal contents.

[Analysis of Crystal Structure of Composite Particles]

Analysis was conducted using model Rint 2500 powder X-ray diffraction apparatus (XRD) manufactured by Rigaku Corp. under conditions of a Cu tube for the X-ray source (40 kV, 200 mA), a measuring range of from 5 to 65 deg (0.02 deg/step), a measuring speed of 0.2 deg/min, and slit widths (scattering, divergence, and reception) of 1 deg, 1 deg, and 0.15 mm.

An approach of uniformly spraying onto a non-reflective sample plate and fixing with neoprene rubber was adopted for samples.

[Analysis of Chemical State of Composite Particle Metal Components]

Analysis was conducted using the model ESCALAB 250 X-ray photoelectron spectroscopy apparatus (XPS) manufactured by Thermo Electron Co., Ltd. under conditions of Al $K\alpha$ at 15 kV×10 mA for the excitation source, an analyzed surface area of about 1 mm (shape: oval), and a 0 to 1,100 eV survey scan and an Ni2p narrow scan for the uptake region.

For measurement samples, the composite particle supported material was crushed in an agate mortar, and collected onto a special-purpose powder sample stage followed by XPS measurement.

[Analysis of Chemical State of Nickel]

Ni $K\alpha$ spectra were measured with model XFRA190 double crystal high-resolution X-ray fluorescence analyzer (HRXRF) manufactured by Technos, and various parameters thus obtained were compared with those of standard substances (nickel metal and nickel oxide) to predict the chemical state such as the valence of nickel in the supported material.

Measurement samples were directly subjected to measurement. The $K\alpha$ spectrum of Ni was measured in the partial spectral mode. In this respect, Ge (220) was used as analyzing crystals. The slit used had a vertical divergence angle of 1°. The excitation voltage and current were set to 35 kV and 80 mA, respectively. Filter paper was then used as an absorber in the case of reference samples, and a counting time was selected for each sample in the case of supported material samples. Measurement was carried out so that the peak intensity of the $K\alpha$ spectra was 3,000 cps or less and 10,000 counts or more. Measurement was repeated five times for each sample, and metal samples were measured before and after each repeated measurement. After smoothing treatment (S-G method, 7 points, 5 times) of the measured spectra, the peak locations, half-width values (FWHM), and asymmetric indices (AI) were calculated, and the peak locations were treated as a chemical shift ($\Delta E$) from the measured value of the metal sample measured before and after measurement of each sample.

[Morphological Observation and Elementary Analysis of Composite Particles]

TEM bright field images, STEM dark field images, and STEM-EDS compositional analyses (point analysis, mapping, and line analysis) were measured using model 3100FEF transmission electron microscope/scanning transmission electron microscope (TEM/STEM) manufactured by JEOL Ltd. [acceleration voltage: 300 kV, with energy dispersive X-ray detector (EDX)].

The data analysis software used was Digital Micrograph™ Ver. 1.70.16 from Gatan, Inc. for TEM image and STEM image analyses (length measurement and Fourier transform analysis), and NORAN System SIX Ver. 2.0 from Thermo Fisher Scientific K.K. for EDS data analyses (mapping image processing and compositional quantification and calculation).

For measurement samples, the composite particle supported material was crushed in a mortar and then dispersed in ethanol. After performing ultrasonic cleaning for about 1 minute, the powder was dropped onto a Mo microgrid and air-dried to obtain TEM/STEM observation samples.

[Measurement of Ultraviolet-Visible Spectra of Composite Particles]

Measurement was carried out using model V-550 ultraviolet-visible spectrophotometer (UV-Vis) manufactured by JASCO Corp. [with integrating sphere unit and powder sample holder] at a measuring range of from 800 to 200 nm and a scanning speed of 400 nm/min.

For measurement samples, the composite particle supported material was crushed in an agate mortar and placed in the powder sample holder followed by UV-Vis measurement.

[Half-Width Wa, Mode Diameter Da, Half-Width Wd, and Mode Diameter Dd of Catalyst]

The pore diameter was measured using Quadrasorb evo from Quantachrome Corp., and using nitrogen as an adsorption gas (nitrogen adsorption). Free space was measured in the "He measure" mode using a reference cell attached to Quadrasorb evo and a 9 mm large bulb as a sample cell, and using pure helium.

Drying for removing moisture from samples was performed under reduced pressure at 200° C. for 18 hours. The amount of each sample was set to 0.1 g. Measurement points were a relative pressure (P/PO) of from 0.025 to 0.9875 for adsorption and a relative pressure of from 0.975 to 0.025 for desorption.

The pore distribution was calculated using the BJH method as to each of adsorption and desorption. For each of adsorption and desorption, a pore diameter (D) was plotted against a value (dV/d(log D)) obtained by differentiating a cumulative pore volume (V) with a common logarithm of the pore diameter (D). When FIG. 3 is taken as an example, mode diameters Da and Dd were defined as a pore diameter at peak top A, and half-widths Wa and Wd were defined as the length from intersections D to E between the pore distribution and a horizontal line drawn at point B where line segment AC of a perpendicular from the peak top to the baseline was bisected.

Example 1

An aqueous solution obtained by dissolving 18.75 parts by mass of aluminum nitrate nonahydrate, 12.8 parts by mass of magnesium nitrate, and 2.7 parts by mass of a 60% by mass nitric acid in 25 parts by mass of pure water was gradually added dropwise into 100 parts by mass of a solution of a silica sol having a colloidal particle diameter of from 10 to 20 nm ($SiO_2$ content: 30% by mass) in a stirred state maintained at 15° C. to obtain a mixed slurry of the silica sol, aluminum nitrate, and magnesium nitrate. Thereafter, the mixed slurry was maintained at 80° C. for 5 hours, then cooled to 30° C., stirred for 5 hours, further heated to 50° C., and maintained for 10 hours, while stirring was continued at a stirring tip speed of 6.5 m/s with a paddle-type stirring blade having a stirring blade diameter of 0.5 m. After cooling to room temperature, the mixed slurry was spray-dried with a spray dryer apparatus set to an outlet temperature at 130° C. to obtain a solid.

Then, the resulting solid was filled to a thickness of about 1 cm into a stainless steel container having an open top, heated in an electric furnace from room temperature to 300° C. over 2 hours, and thereafter held for 3 hours. Further, after heated to 600° C. over 2 hours and held for 3 hours, the solid was cooled to obtain a support. The resulting support contained silicon, aluminum, and magnesium at 83.3 mol %, 8.3 mol %, and 8.3 mol %, respectively, based on the total molar amount of the silicon, the aluminum, and the magnesium. The support had a specific surface area of 149 $m^2$/g, a pore volume of 0.27 mL/g, and an average pore diameter of 7 nm, according to nitrogen adsorption. The average particle diameter of the support was 60 μm based on the results of measurement of laser diffraction/scattering particle size distribution. The form of the support was determined to be nearly spherical based on observations using a scanning electron microscope (SEM).

300 g of the support obtained as described above was added over 1 minute to 1.0 L of water heated to 90° C., then dispersed, and stirred at 90° C. for 15 minutes. Next, an aqueous solution containing 16.35 g of nickel nitrate hexahydrate and 12 mL of a 1.3 mol/L aqueous chloroauric acid solution was prepared and heated to 90° C., and the resulting solution was added to the support slurry and further stirred at 90° C. for 30 minutes to thereby insolubly immobilize the nickel and gold component onto the support.

Then, after removing the supernatant by allowing to stand and washing several times with distilled water, the washed resultant was filtered. This filtered residue was dried with a drier at 105° C. for 10 hours and fired at 450° C. in air for 5 hours in a muffle furnace to obtain a catalyst for production of carboxylic acid ester supporting 1.05% by mass nickel and 0.91% by mass gold (composite particle supported material of $NiOAu/SiO_2$—$Al_2O_3$—MgO). The Ni/Au atomic ratio in the composite particles contained in the resulting catalyst for production of carboxylic acid ester was 4.0.

(Evaluation of Physical Properties of Catalyst for Production of Carboxylic Acid Ester)

The specific surface area of the resulting catalyst for production of carboxylic acid ester was determined and was consequently 141 $m^2$/g. As a result of obtaining pore distributions, the half-width of pore distribution of adsorption was 5 nm, and the half-width of pore distribution of desorption was 2 nm.

Then, samples obtained by embedding the resulting catalyst for production of carboxylic acid ester in a resin and polishing were subjected to ray analysis of particle cross sections using an X-ray microprobe (SPMA). It was confirmed that: a region from the outermost surface of the support to a depth of 0.5 μm had an outer layer substantially free of nickel and gold; nickel and gold were supported in a region from the surface to a depth of 10 μm; and composite particles were absent inside the support.

Next, as a result of observing the form of the catalyst for production of carboxylic acid ester under a transmission electron microscope (TEM/STEM), it was confirmed that spherical nanoparticles having a local maximum distribution at a particle diameter of from 2 to 3 nm (number average particle diameter: 3.0 nm) were supported by the support. When the nanoparticles were further observed by magnification, lattice fringes corresponding to Au (111) plane spacings were observed in the nanoparticles. As a result of conducting compositional point analysis on individual nanoparticles by STEM-EDS, nickel and gold were detected in all the particles. The average nickel/gold atomic ratio (the number of particles for calculation: 50) of the nanoparticles was 1.05. As a result of further conducting nanoregion analysis of the observed particles, the Ni/Au atomic ratio was 0.90 for the central portions of the particles and 2.56 for the edges of the particles. Only nickel was detected in a very small amount in portions other than the particles. As a result of carrying out similar measurement at 50 points, nickel was detected in a large amount at or near the edges of all the particles. From EDS element mapping, close agreement between the distributions of nickel and gold was observed. From line profiling of the composition, nickel was distributed slightly larger than the distribution of gold in all the directions of scanning.

From the results of powder X-ray diffraction (XRD), no diffraction pattern derived from nickel was observed, confirming that nickel was present in an amorphous state. On the other hand, there existed a broad peak, albeit not being a clear peak, corresponding to crystals of gold. The average crystallite diameter thereof was calculated according to the Scherrer equation and was consequently on the order of 3 nm, which was a value close to the detection limit (2 nm) of the powder X-ray diffraction. As for the chemical state of nickel, the nickel was confirmed to be divalent on the basis of the results of X-ray photoelectron spectroscopy (XPS).

From the results of the double crystal high-resolution X-ray fluorescence method (HRXRF), it was presumed that the chemical state of nickel was a high-spin state of divalent nickel, and difference in the $NiK\alpha$ spectrum revealed that the chemical state differed from that of nickel oxide as a single compound. The catalyst had a $NiK\alpha$ spectrum half-width (FWHM) of 3.470 and a chemical shift ($\Delta E$) of 0.335 on the basis of the measured spectra. The nickel oxide measured as a reference substance had a $NiK\alpha$ spectrum half-width (FWHM) of 3.249 and a chemical shift ($\Delta E$) of 0.344.

As a result of examining the excited state of electrons in this catalyst for production of carboxylic acid ester by ultraviolet-visible spectroscopy (UV-Vis), no surface plasmon absorption peak derived from gold nanoparticles around 530 nm appeared, and broad absorption caused by $NiO_2$ was confirmed in a wavelength region of from 200 to 800 nm.

From the above results, it is presumed that the fine structure of the composite particles has a form in which the gold nanoparticles serve as the core and the surface thereof is coated with oxidized nickel.

(Production of Carboxylic Acid Ester)

240 g of the resulting catalyst for production of carboxylic acid ester was placed into a stirred stainless steel reactor having a catalyst separator and a liquid phase portion of 1.2 liters followed by carrying out an oxidative carboxylic acid ester formation reaction from an aldehyde and an alcohol while stirring the contents at a tip speed of the stirrer blade of 4 m/s. A solution of 36.7% by mass methacrolein in methanol (a methanol solution having a moisture content of 0.50% by mass was used) at 0.6 liters/hr and a solution of 1 to 4% by mass NaOH in methanol at 0.06 liters/hr were continuously supplied to the reactor, air was blown in at a reaction temperature of 80° C. and a reaction pressure of 0.5 MPa such that the outlet oxygen concentration was 4.0 vol % (equivalent to the oxygen partial pressure of 0.02 MPa), and the concentration of NaOH supplied to the reactor was controlled such that a pH of the reaction system was 7. The reaction product was continuously extracted from the reactor outlet by overflow, and the reactivity was investigated by analyzing by gas chromatography.

At 500 hours after the start of the reaction, the methacrolein conversion rate was 75.2%, and the selectivity of methyl methacrylate was 98.1%.

(Durability Test)

Next, in order to evaluate the acid resistance, base resistance, and temperature resistance of the catalyst for production of carboxylic acid ester, the durability test was conducted by the following method. 10 g of the unused catalyst for production of carboxylic acid ester obtained as described above was added to 100 mL of a buffer solution of pH 4 placed in a glass container, and stirred at 90° C. for 10 minutes followed by removing the supernatant by allowing to stand, washing with water, and decantation. The solid thus obtained was added to 100 mL of a buffer solution of pH 10 placed in a glass container, and stirred at 90° C. for 10 minutes followed by removing the supernatant by allowing to stand, washing with water, and decantation. The above operation was defined as one cycle, and 100 cycles in total of treatments were carried out. The half-width of pore distribution was determined in the same manner as above as to the catalyst for production of carboxylic acid ester after this durability test. The production of carboxylic acid ester was further carried out for 500 hours in the same manner as above as to the whole amount of the catalyst for production of carboxylic acid ester after the durability test, and the methacrolein conversion rate and the selectivity of methyl methacrylate were determined. These results are also shown in Table 1.

Comparative Example 1

A catalyst for production of carboxylic acid ester was obtained in the same manner as in Example 1 except that: the stirring conditions of the mixed slurry before spray drying with a spray dryer apparatus involved stirring at a stirring tip speed of 1.3 m/s (100 rpm) with an anchor-type stirring blade having a stirring blade diameter of 0.2 m; and the hydrothermal synthesis conditions at the time of support preparation were changed to the conditions shown in the table. The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Example 2

(Production of Catalyst for Production of Carboxylic Acid Ester)

300 g of the support obtained in Example 1 was added over 1 minute to 1.0 L of water heated to 90° C., then dispersed, and stirred at 90° C. for 15 minutes. Next, an aqueous solution containing 16.36 g of cobalt nitrate hexahydrate and 12 mL of a 1.3 mol/L aqueous chloroauric acid solution was prepared and heated to 90° C., and the resulting solution was added to the support slurry and further stirred at 90° C. for 30 minutes to thereby insolubly immobilize the cobalt and gold component onto the support.

Then, after removing the supernatant by allowing to stand and washing several times with distilled water, the washed resultant was filtered. This filtered residue was dried with a drier at 105° C. for 10 hours and fired at 400° C. in air for 5 hours in a muffle furnace to obtain a catalyst for production of carboxylic acid ester supporting 1.05% by mass cobalt and 0.91% by mass gold (composite particle supported material of $CoAu/SiO_2$—$Al_2O_3$—MgO). The Co/Au atomic ratio of the resulting catalyst for production of carboxylic acid ester was 4.0.

(Evaluation of Physical Properties of Catalyst for Production of Carboxylic Acid Ester)

The specific surface area of the resulting catalyst for production of carboxylic acid ester was determined and was consequently 139 m²/g. As a result of obtaining pore distributions, the half-width Wa of pore distribution of adsorption was 5 nm, and the half-width Wd of pore distribution of desorption was 3 nm.

(Production of Carboxylic Acid Ester)

240 g of the resulting catalyst for production of carboxylic acid ester was placed into a stirred stainless steel reactor having a catalyst separator and a liquid phase portion of 1.2 liters followed by carrying out an oxidative carboxylic acid ester formation reaction from an aldehyde and an alcohol while stirring the contents at a tip speed of the stirrer blade of 4 m/s. A solution of 36.7% by mass methacrolein in methanol (a methanol solution having a moisture content of 0.50% by mass was used) at 0.6 liters/hr and a solution of 1 to 4% by mass NaOH in methanol at 0.06 liters/hr were continuously supplied to the reactor, air was blown in at a reaction temperature of 80° C. and a reaction pressure of 0.5 MPa such that the outlet oxygen concentration was 4.0 vol % (equivalent to the oxygen partial pressure of 0.02 MPa), and the concentration of NaOH supplied to the reactor was controlled such that a pH of the reaction system was 7. The reaction product was continuously extracted from the reactor outlet by overflow, and the reactivity was investigated by analyzing by gas chromatography.

At 500 hours after the start of the reaction, the methacrolein conversion rate was 74.5%, and the selectivity of methyl methacrylate was 97.8%.

Next, the durability test was conducted by the method described in Example 1. The results are shown in Table 1.

Example 3

A support was obtained by the same method as in Example 1 except that the stirring conditions of the mixed slurry before spray drying with a spray dryer apparatus involved stirring at a stirring tip speed of 6.5 m/s with a turbine-type stirring blade having a stirring blade diameter of 0.5 m. Thereafter, a catalyst for production of carboxylic acid ester was obtained by the same method as in Example 1 except that 300 g of the support was added over 1 minute to 1.0 L of water heated to 90° C., then dispersed, and stirred at 90° C. for 30 minutes. The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Example 4

A catalyst for production of carboxylic acid ester was obtained in the same manner as in Example 1 except that 300 g of the support obtained in Example 1 was added over 1 minute to 1.0 L of water heated to 90° C., then dispersed, and stirred at 90° C. for 10 minutes. The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Comparative Example 2

A support was obtained in the same manner as in Comparative Example 1, and a catalyst for production of carboxylic acid ester was further obtained in the same manner as in Example 2. The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Comparative Example 3

A catalyst for production of carboxylic acid ester was obtained in the same manner as in Example 3 except that 300 g of the support obtained in Comparative Example 1 was added over 1 minute to 1.0 L of water heated to 90° C., then dispersed, and stirred at 90° C. for 30 minutes. The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Example 5

An aqueous solution obtained by dissolving aluminum nitrate, magnesium nitrate, and 2.7 parts by mass of a 60% by mass nitric acid in 25 parts by mass of pure water such that the amounts of aluminum and magnesium to be contained in a support would be 36.6 mol % and 17.2 mol % respectively, based on the total molar amount of silicon, aluminum, and magnesium was gradually added dropwise into 100 parts by mass of a solution of a silica sol having a colloidal particle diameter of from 10 to 20 nm (SiO₂ content: 30% by mass) in a stirred state maintained at 15° C. to obtain a mixed slurry of the silica sol, aluminum nitrate, and magnesium nitrate. Thereafter, the mixed slurry was maintained at 80° C. for 5 hours, then cooled to 30° C., stirred for 5 hours, further heated to 50° C., and maintained for 10 hours, while stirring was continued at a stirring tip speed of 6.5 m/s with a paddle-type stirring blade having a stirring blade diameter of 0.5 m. After cooling to room temperature, the mixed slurry was spray-dried with a spray dryer apparatus set to an outlet temperature at 130° C. to obtain a solid.

Then, the resulting solid was filled to a thickness of about 1 cm into a stainless steel container having an open top, heated in an electric furnace from room temperature to 300° C. over 2 hours, and thereafter held for 3 hours. Further, after heated to 800° C. over 2 hours and held for 3 hours, the solid was cooled to obtain a support. The average particle diameter of the support was 64 μm based on the results of measurement of laser diffraction/scattering particle size distribution. The form of the support was determined to be nearly spherical based on observations using a scanning electron microscope (SEM).

300 g of the support obtained as described above was added over 3 minutes to 1.0 L of water heated to 85° C., then dispersed, and stirred at 85° C. for 10 minutes.

Next, an aqueous solution containing 16.35 g of nickel nitrate hexahydrate and 13 mL of a 1.3 mol/L aqueous chloroauric acid solution was prepared and heated to 85° C., and the resulting solution was added to the slurry and further stirred at 85° C. for 30 minutes to thereby precipitate the nickel and gold component onto the support.

Then, after removing the supernatant by allowing to stand and washing several times with distilled water, the washed resultant was filtered. This filtered residue was dried at 105° C. for 16 hours and fired at 500° C. in air for 3 hours to obtain a catalyst for production of carboxylic acid ester supporting 1.0% by mass nickel and 0.90% by mass gold (NiOAu/SiO₂—Al₂O₃—MgO). The Ni/Au atomic ratio in the composite particles contained in the resulting catalyst for production of carboxylic acid ester was 3.7. The average particle diameter of the catalyst was 65 based on the results of measurement of laser diffraction/scattering particle size distribution. The form of the support was determined to be nearly spherical based on observations using a scanning electron microscope (SEM).

Wa was 6 nm, and Wd was 7 nm. As a result of observing the form of the active species of this catalyst under a transmission electron microscope (TEM/STEM), it was confirmed that nanoparticles having a local maximum distribution at a particle diameter of from 2 to 3 nm (number average particle diameter: 3.3 nm) were supported by the support.

The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Example 6

300 g of the support obtained in Example 1 was added over 1 minute to 1.0 L of water heated to 90° C., then dispersed, and stirred at 90° C. for 15 minutes. Thereafter, the temperature was decreased to 60° C., and a dilute hydrochloric solution of palladium chloride and an aqueous lead nitrate solution in amounts corresponding to 2.5% by mass as Pd and Pb, respectively, were quickly added thereto while stirred. Thereafter, the mixture was maintained at 60° C. for 1 hour, and reduced by adding hydrazine thereto in an amount of 1.2 times the stoichiometric amount. Then, after removing the supernatant by allowing to stand and washing several times with distilled water, the washed resultant was filtered. This filtered residue was further dried in vacuum at 60° C. to obtain a catalyst for production of carboxylic acid ester supporting 2.5% by mass each of Pd and Pb (composite particle supported material of PdPb/SiO₂—Al₂O₃—MgO).

According to the results of powder X-ray diffraction (XRD) of the noble metal supported material, diffraction peaks (2θ=38.6°, 44.8°, 65.4°, and 78.6°) attributed to an intermetallic compound of Pd3Pb1 were observed.

The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Comparative Example 4

A catalyst for production of carboxylic acid ester was obtained in the same manner as in Example 6 except that: the stirring conditions of the mixed slurry before spray drying with a spray dryer apparatus involved stirring at a stirring tip speed of 1.3 m/s with an anchor-type stirring blade having a stirring blade diameter of 0.2 m; and the hydrothermal synthesis conditions at the time of support preparation were changed to the conditions shown in the table. The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Example 7

A catalyst for production of carboxylic acid ester was obtained in the same manner as in Example 6 except that: 300 g of the support obtained in Example 1 was added over 3 minutes to 1.0 L of water heated to 90° C., then dispersed, and stirred at 85° C. for 10 minutes; and thereafter, the temperature was decreased to 60° C. The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Example 8

A catalyst for production of carboxylic acid ester was obtained in the same manner as in Example 1 except that the hydrothermal synthesis conditions at the time of support preparation were changed to the conditions shown in the table. The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Example 9

A catalyst for production of carboxylic acid ester was obtained in the same manner as in Example 8 except that the stirring conditions of the mixed slurry before spray drying with a spray dryer apparatus were changed to a stirring tip speed of 10.2 m/s. The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Example 10

A catalyst for production of carboxylic acid ester was obtained in the same manner as in Example 8 except that the stirring conditions of the mixed slurry before spray drying with a spray dryer apparatus involved stirring at a stirring tip speed of 6.5 m/s with a turbine-type stirring blade having a stirring blade diameter of 0.5 m. The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Example 11

An aqueous solution was prepared by dissolving 1.5 parts by mass of aluminum nitrate nonahydrate, 0.24 parts by mass of nickel nitrate hexahydrate, 0.98 parts by mass of magnesium nitrate hexahydrate, and 0.27 parts by mass of a 60% by mass nitric acid in 3.0 parts by mass of pure water.

A silica-containing support was obtained in the same manner as in Example 1 except that the aqueous solution was gradually added dropwise into 100 parts by mass of a solution of a silica sol having a colloidal particle diameter of from 10 to 20 nm ($SiO_2$ content: 30% by mass) in a stirred state maintained at 15° C. to obtain a mixed slurry of the silica sol, aluminum nitrate, nickel nitrate, and magnesium nitrate.

The resulting silica-containing support contained 85.3 mol % of silicon, 6.8 mol % of aluminum, 1.4 mol % of nickel, and 6.5 mol % of magnesium, based on the total molar amount of silicon, aluminum, nickel, and magnesium.

A catalyst for production of carboxylic acid ester (composite particle supported material of $NiOAu/SiO_2$—$Al_2O_3$—NiO—MgO) was obtained in the same manner as in Example 1 using the silica-containing support. The Ni/Au atomic ratio in the composite particles contained in the resulting catalyst for production of carboxylic acid ester was 4.0.

The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

Example 12

A catalyst for production of carboxylic acid ester was obtained in the same manner as in Example 1 except that 300 g of the support obtained in Example 1 was added over 3 minutes to 1.0 L of water heated to 95° C., then dispersed, and stirred at 95° C. for 15 minutes. The durability test described above was carried out as to the catalyst for production of carboxylic acid ester, and the half-width of pore distribution, the methacrolein conversion rate, and the selectivity of methyl methacrylate were determined before and after the test in the same manner as in Example 1. These results are shown in Table 1.

TABLE 1

| | Composition and production conditions | | | | | | | | | |
|---|---|---|---|---|---|---|---|---|---|---|
| | Composition of support | Nanoparticles | Hydrothermal synthesis conditions at time of support preparation | | | Tip speed (m/s) | Stirring blade shape | Duration of addition of support [min] | Duration of water dispersion of support |
| Example 1 | Si-Al-Mg | NiOAu | 80° C./5 h | 30° C./5 h | 50° C./10 h | 6.5 | Paddle | 1 | 90° C./15 min |
| Example 2 | Si-Al-Mg | CoOAu | 80° C./5 h | 30° C./5 h | 50° C./10 h | 6.5 | Paddle | 1 | 90° C./15 min |
| Example 3 | Si-Al-Mg | NiOAu | 80° C./5 h | 30° C./5 h | 50° C./10 h | 6.5 | Turbine | 1 | 90° C./30 min |
| Example 4 | Si-Al-Mg | NiOAu | 80° C./5 h | 30° C./5 h | 50° C./10 h | 6.5 | Paddle | 1 | 90° C./10 min |
| Example 5 | Si-Al-Mg | NiOAu | 80° C./5 h | 30° C./5 h | 50° C./10 h | 6.5 | Paddle | 3 | 85° C./10 min |
| Example 6 | Si-Al-Mg | PdPb | 80° C./5 h | 30° C./5 h | 50° C./10 h | 6.5 | Paddle | 1 | 90° C./15 min |
| Example 7 | Si-Al-Mg | PdPb | 80° C./5 h | 30° C./5 h | 50° C./10 h | 6.5 | Paddle | 3 | 85° C./10 min |
| Example 8 | Si-Al-Mg | NiOAu | | 50° C./24 h | | 6.5 | Paddle | 1 | 90° C./15 min |
| Example 9 | Si-Al-Mg | NiOAu | | 50° C./24 h | | 10.2 | Paddle | 1 | 90° C./15 min |
| Example 10 | Si-Al-Mg | NiOAu | | 50° C./24 h | | 6.5 | Turbine | 1 | 90° C./15 min |
| Example 11 | Si-Al-Mg-Ni | NiOAu | 80° C./5 h | 30° C./5 h | 50° C./10 h | 6.5 | Paddle | 1 | 90° C./15 min |
| Example 12 | Si-Al-Mg | NiOAu | 80° C./5 h | 30° C./5 h | 50° C./10 h | 6.5 | Paddle | 3 | 95° C./15 min |
| Comparative Example 1 | Si-Al-Mg | NiOAu | | 50° C./24 h | | 1.3 | Anchor | 1 | 90° C./15 min |
| Comparative Example 2 | Si-Al-Mg | CoOAu | | 50° C./24 h | | 1.3 | Anchor | 1 | 90° C./15 min |
| Comparative Example 3 | Si-Al-Mg | NiOAu | | 50° C./24 h | | 1.3 | Anchor | 1 | 90° C./30 min |
| Comparative Example 4 | Si-Al-Mg | PdPb | | 50° C./24 h | | 1.3 | Anchor | 1 | 90° C./15 min |

| | Before durability test | | | | After durability test (100 cycles of pH swing) | | | |
|---|---|---|---|---|---|---|---|---|
| | Pore distribution | | Reaction results (500 hours later) | | Pore distribution | | Reaction results (500 hours later) | |
| | Wa [nm] | Wd [nm] | Macr conversion rate [%] | Selectivity of MMA [%] | Wa [nm] | Wd [nm] | Macr conversion rate [%] | Selectivity of MMA [%] |
| Example 1 | 5 | 2 | 75.2 | 98.1 | 6 | 3 | 73.8 | 95.6 |
| Example 2 | 5 | 3 | 74.5 | 97.8 | 7 | 5 | 72.1 | 95.0 |
| Example 3 | 4 | 2 | 75.0 | 98.5 | 4 | 3 | 74.5 | 96.2 |
| Example 4 | 6 | 4 | 75.2 | 97.9 | 7 | 5 | 72.9 | 95.0 |
| Example 5 | 6 | 7 | 73.4 | 97.1 | 7 | 8 | 69.9 | 92.9 |
| Example 6 | 6 | 4 | 65.1 | 83.3 | 9 | 6 | 60.2 | 77.8 |
| Example 7 | 6 | 7 | 62.6 | 82.1 | 9 | 9 | 57.1 | 76.3 |
| Example 8 | 7 | 2 | 75.0 | 97.6 | 9 | 3 | 70.5 | 93.7 |
| Example 9 | 5 | 2 | 75.4 | 97.7 | 6 | 3 | 72.2 | 94.6 |
| Example 10 | 6 | 2 | 75.2 | 97.2 | 7 | 3 | 71.3 | 94.0 |
| Example 11 | 5 | 2 | 73.1 | 96.8 | 5 | 3 | 72.6 | 94.9 |
| Example 12 | 5 | 4 | 75.2 | 98.0 | 6 | 5 | 73.2 | 95.3 |
| Comparative Example 1 | 13 | 2 | 75.4 | 97.2 | 20 | 6 | 63.4 | 85.2 |

TABLE 1-continued

| | | | | | | | | |
|---|---|---|---|---|---|---|---|---|
| Comparative Example 2 | 13 | 3 | 74.3 | 96.4 | 23 | 8 | 61.2 | 84.0 |
| Comparative Example 3 | 12 | 2 | 75.3 | 97.4 | 18 | 6 | 65.1 | 87.2 |
| Comparative Example 4 | 14 | 5 | 63.9 | 82.3 | 25 | 9 | 49.1 | 67.8 |

| | Difference between before and after durability test | | | | Percent change between before and after durability test | |
|---|---|---|---|---|---|---|
| | | | | | Rate of change in | Rate of change in |
| | Wa [nm] | Wd [nm] | Macr conversion rate [%] | Selectivity of MMA [%] | Macr conversion rate [%] | selectivity of MMA [%] |
| Example 1 | 1 | 1 | −1.4 | −2.5 | −1.9 | −2.5 |
| Example 2 | 2 | 2 | −2.4 | −2.8 | −3.2 | −2.9 |
| Example 3 | 0 | 1 | −0.5 | −2.3 | −0.7 | −2.3 |
| Example 4 | 1 | 1 | −2.3 | −2.9 | −3.1 | −3.0 |
| Example 5 | 1 | 1 | −3.5 | −4.2 | −4.8 | −4.3 |
| Example 6 | 3 | 2 | −4.9 | −5.5 | −7.5 | −6.6 |
| Example 7 | 3 | 2 | −5.5 | −5.8 | −8.8 | −7.1 |
| Example 8 | 2 | 1 | −4.5 | −3.9 | −6.0 | −4.0 |
| Example 9 | 1 | 1 | −3.2 | −3.1 | −4.2 | −3.2 |
| Example 10 | 1 | 1 | −3.9 | −3.2 | −5.2 | −3.3 |
| Example 11 | 0 | 1 | −0.5 | −1.9 | −0.7 | −2.0 |
| Example 12 | 1 | 1 | −2.0 | −2.7 | −2.7 | −2.8 |
| Comparative Example 1 | 7 | 4 | −12.0 | −12.0 | −15.9 | −12.3 |
| Comparative Example 2 | 10 | 5 | −13.1 | −12.4 | −17.6 | −12.9 |
| Comparative Example 3 | 6 | 4 | −10.2 | −10.2 | −13.5 | −10.5 |
| Comparative Example 4 | 11 | 4 | −14.8 | −14.5 | −23.2 | −17.6 |

Macr: Methacrolein,
MMA: Methyl methacrylate

The invention claimed is:

1. A catalyst for production of carboxylic acid ester, comprising:
   catalyst particles comprising at least one element selected from the group consisting of nickel, cobalt, palladium, lead, platinum, ruthenium, gold, silver, and copper; and
   a support supporting the catalyst particles, wherein
   the catalyst for production of carboxylic acid ester has a half-width Wa of pore distribution of 10 nm or less, the half-width Wa being calculated using BJH method from an adsorption isotherm obtained by nitrogen adsorption.

2. The catalyst for production of carboxylic acid ester according to claim 1, wherein the catalyst for production of carboxylic acid ester has a half-width Wd of pore distribution of 5 nm or less, the half-width Wd being calculated using BJH method from a desorption isotherm obtained by nitrogen adsorption.

3. The catalyst for production of carboxylic acid ester according to claim 1, wherein the catalyst for production of carboxylic acid ester has a pore mode diameter Da of 2 nm or more and 20 nm or less, the pore mode diameter Da being calculated using BJH method from an adsorption isotherm obtained by nitrogen adsorption.

4. The catalyst for production of carboxylic acid ester according to claim 1, wherein the pore mode diameter Da and the half-width Wa of the catalyst for production of carboxylic acid ester, the pore mode diameter Da and the half-width Wa being calculated using BJH method from the adsorption isotherm obtained by nitrogen adsorption, satisfy a relationship of the following expression (1):

$$\tfrac{1}{2}Wa < Da \qquad (1).$$

5. The catalyst for production of carboxylic acid ester according to claim 1, wherein the catalyst for production of carboxylic acid ester has a pore mode diameter Dd of 2 nm or more and 15 nm or less, the pore mode diameter Dd being calculated using BJH method from a desorption isotherm obtained by nitrogen adsorption.

6. The catalyst for production of carboxylic acid ester according to claim 1, wherein a pore mode diameter Dd of the catalyst for production of carboxylic acid ester, the pore mode diameter Dd being calculated using BJH method from a desorption isotherm obtained by nitrogen adsorption, and a half-width Wd of pore distribution of the catalyst for production of carboxylic acid ester, the half-width Wd being calculated using BJH method from a desorption isotherm obtained by nitrogen adsorption, satisfy a relationship of the following expression (2):

$$\tfrac{1}{2}Wd < Dd \qquad (2).$$

7. The catalyst for production of carboxylic acid ester according to claim 1, wherein the half-width Wa is 0.1 nm or more.

8. The catalyst for production of carboxylic acid ester according to claim 1, wherein the catalyst particles comprise at least one element selected from the group consisting of nickel, cobalt, palladium, lead, and gold.

9. The catalyst for production of carboxylic acid ester according to claim 1, wherein the catalyst particles are composite particles comprising:
   oxidized nickel and/or cobalt, and
   X, wherein X represents at least one element selected from the group consisting of nickel, palladium, platinum, ruthenium, gold, silver, and copper.

10. The catalyst for production of carboxylic acid ester according to claim 9, wherein a compositional ratio between nickel or cobalt and X in the composite particles, in terms of a Ni/X atomic ratio or a Co/X atomic ratio, is 0.1 or more and 10 or less.

11. The catalyst for production of carboxylic acid ester according to claim 9, wherein the composite particles comprise oxidized nickel and gold.

12. The catalyst for production of carboxylic acid ester according to claim 10, wherein a compositional ratio between nickel and gold in the composite particles, in terms of a Ni/Au atomic ratio, is 1.1 or more and 10 or less.

13. The catalyst for production of carboxylic acid ester according to claim 1, wherein the catalyst particles have an average particle diameter of 2 nm or more and 10 nm or less.

14. The catalyst for production of carboxylic acid ester according to claim 1, wherein the support is a support composed of aluminum-containing silica-based composition comprising silica and alumina.

15. The catalyst for production of carboxylic acid ester according to claim 1, wherein the support is a silica-based material comprising:
  silicon,
  aluminum,
  at least one period 4 element selected from the group consisting of iron, cobalt, nickel, and zinc, and
  at least one basic element selected from the group consisting of an alkali metal element, an alkaline earth metal element, and a rare earth element, wherein
  contents thereof are in ranges of 42 mol % or more and 90 mol % or less, 3 mol % or more and 38 mol % or less, 0.5 mol % or more and 20 mol % or less, and 2 mol % or more and 38 mol % or less, respectively, based on a total molar amount of the silicon, the aluminum, the period 4 element, and the basic element.

16. The catalyst for production of carboxylic acid ester according to claim 1, wherein a supported layer in which the catalyst particles are localized is present in a region extending from a surface of the catalyst for production of carboxylic acid ester to 40% of an equivalent diameter of the catalyst for production of carboxylic acid ester.

17. The catalyst for production of carboxylic acid ester according to claim 1, wherein the catalyst for production of carboxylic acid ester has an equivalent diameter of 200 μm or less, and a supported layer in which the catalyst particles are localized is present in a region extending from the surface of the catalyst for production of carboxylic acid ester to 30% of the equivalent diameter of the catalyst for production of carboxylic acid ester.

18. The catalyst for production of carboxylic acid ester according to claim 1, wherein the catalyst for production of carboxylic acid ester has an outer layer substantially free of catalyst particles on an outside of the supported layer in which the catalyst particles are localized, and the outer layer is formed at a thickness of 0.01 μm or more and 15 μm or less.

19. The catalyst for production of carboxylic acid ester according to claim 9, wherein the catalyst particles have a core composed of X, and the core is coated with oxidized nickel and/or cobalt.

20. A method for producing carboxylic acid ester comprising a reaction step of reacting (a) an aldehyde and an alcohol or (b) one or two or more alcohols, in a presence of the catalyst for production of carboxylic acid ester according to claim 1 and oxygen.

21. The method for producing carboxylic acid ester according to claim 20, wherein the aldehyde is acrolein and/or methacrolein.

22. The method for producing carboxylic acid ester according to claim 20, wherein the aldehyde is acrolein and/or methacrolein, and the alcohol is methanol.

23. The method for producing carboxylic acid ester according to claim 20, wherein the reaction step is performed in a liquid phase.

24. The method for producing carboxylic acid ester according to claim 20, wherein the reaction step is performed while a basic substance is added so that pH of the reaction system is 6 or more and 8 or less.

\* \* \* \* \*